United States Patent [19]

Jähne et al.

[11] Patent Number: 5,631,259
[45] Date of Patent: May 20, 1997

[54] CYCLOALKLTRIOLS CONTAINING CYCLIC SUBSTITUENTS, PROCESSES AND INTERMEDIATE PRODUCTS FOR THEIR PREPARATION AND THEIR USE AS ANTIVIRAL AND ANTIPARASITIC AGENTS

[75] Inventors: Gerhard Jähne, Frankfurt am Main; Irvin Winkler, Liederbach; Matthias Helsberg, Kelkheim; Heinz Hänel, Oberursel, all of Germany

[73] Assignee: Hoechst Aktiengesellschaft, Frankfurt am Main, Germany

[21] Appl. No.: 466,883

[22] Filed: Jun. 6, 1995

Related U.S. Application Data

[63] Continuation of Ser. No. 907,571, Jul. 2, 1992, abandoned.

[30] Foreign Application Priority Data

Jul. 4, 1991 [DE] Germany ............ 41 22 068.4

[51] Int. Cl.$^6$ ............ A61K 31/52; C07D 473/30; C07D 473/34; C07D 473/18
[52] U.S. Cl. ............ 514/261; 514/262; 544/239; 544/241; 544/262; 544/264; 544/265; 544/276; 544/277; 544/314; 544/317; 544/318; 546/118; 546/301; 548/266.8; 548/268.6; 548/304.4; 548/331.1; 548/473; 548/545; 548/548
[58] Field of Search ............ 544/229, 264, 544/265, 266, 267, 268, 271, 272, 273, 276, 277; 514/263, 262, 261, 265, 260

[56] References Cited

FOREIGN PATENT DOCUMENTS

| | | |
|---|---|---|
| 0369409 | 5/1990 | European Pat. Off. . |
| 0368640 | 5/1990 | European Pat. Off. . |
| 0475413 | 3/1992 | European Pat. Off. . |
| WO91/15489 | 10/1991 | WIPO . |

OTHER PUBLICATIONS

Cecil Textbook of Medicine, 19th Edition p. 1844 (1992).
Patil, J Med Chem 35, 3374 (1992).
Kizilisik, Transplantation Proc. 25, 2282 (1993).
Edman, Nature 334, 519 (1988).
Barry M. Trost, Gee–Hong Kuo & Torre Benneche: "A Transition–Metal–Controlled Synthesis of (±)–Aristeromycin and (±)–2',3'–diepi–Aristeromycin. An Unusual Directive Effect in Hydroxylations," J. Am. Chem. Soc., vol. 110, pp. 621–622 (1988).
Sharadbala D. Patil & Stewart W. Schneller: "(±)–5'–Nor Ribofuranoside Carbocyclic Guanosine"; Journal of Heterocyclic Chemistry, vol. 28, No. 3, pp. 823–825 (1991).
Chemical Abstracts; American Chemical Society, vol. 109, N. 11, p. 701 (Sep. 12, 1988) 92898u.
Chemical Abstracts: American Chemical Society, vol. 112, N. 21, p. 263, (May 21, 1990) 193759s.
Chemical Abstracts: American Chemical Society, vol. 99, N. 5, p. 490, (Aug. 1, 1983) 38081j.
Chemical Abstracts: American Chemical Society, vol. 83, No. 25, p. 352, (Dec. 22, 1975). 205806c.
Chemical Abstracts: American Chemical Society, vol. 86, No. 5, p. 329, (Jan. 31, 1977) 29396v.
Chemical Abstracts: American Chemical Society, vol. 96, No. 13, p. 657, (Mar. 29, 1982) 10370o.
Diane M. Coe, et al., "Synthesis of Some Mimics of Nucleoside Triphosphates"; J. Chem. Soc. Chem. Commun., pp. 312–314 (Mar. 1, 1991).
Micheal R. Peel, Daniel D. Sternbach & M. Ross Johnson: "A Short, Enantioselective Synthesis of the Carbocyclic Nucleoside Carbovir"; The Journal of Organic Chemistry; The American Chemical Society, vol. 56, No. 16, pp. 4490–4493 (1991).
Diane M. Coe, David C. Orr, Stanley M. Roberts & Richard Storerside: "Preparation of Nucleotide Mimics with Potent Inhibitory Activity Against HIV Reverse Transcriptase"; Journal of the Chemical Society, Perkin Transactions 1, No. 12, pp. 3378–3379 (Dec. 1991).
Merck Index, 11th Edition, 1989, p. 1017.
Hawley's Condensed Chemical Dictionary, 11th Edition (1990) p. 21.
Resolution of Aristeromycin Enantiomers, J. Med. Chem., vol. 28, pp. 1385–1386, 1985.
De Clercq, "Antiviral and Antimetabolic Activities of Neplanocins", Anti–microbial Agents and Chemotherapy, vol. 28, No. 1, pp. 84–89, Jul. 1985.
Hasobe et al., "Elucidation of the Mechanism by which Homocysteine Potentiates the Anti–Vaccinia Virus Effects of the S–Adenosylhomocysteine Hydrolase Inhibitor 9–(trans–2', trans–3'–Dihydroxycyclopent–4'–enyl)–adenine", Molecular Pharmacology, vol. 36, pp. 490–496, Jun. 1989.
Trost et al. "A Transition–Metal–Controlled Synthesis of (±)–Aristeromycin and (±)–2', 3'–diepi–Aristeromycin: An Unusual Directive Effect in Hydroxylations", J. Am. Chem. Soc., vol. 110, pp. 621–622, 1988.
Marquez et al., Carbocyclic Nucleosides, Medicinal Research Reviews, vol. 6 No. 1, pp. 1–40, 1986.

Primary Examiner—Mark L. Berch
Attorney, Agent, or Firm—Finnegan, Henderson, Farabow, Garrett & Dunner, L.L.P.

[57] ABSTRACT

Cycloalkyltriols containing heterocyclic substituents, in particular cyclopentyl- and cyclohexyltriols containing heterocyclic substituents Compounds of the formulae I and II

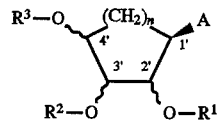

Formula I

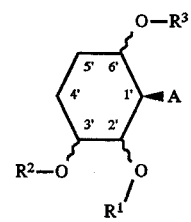

Formula II in which the substituents A, $R^1$, $R^2$ and $R^3$ and n have the meanings given, have an antiviral and antiparasitic action.

2 Claims, No Drawings

CYCLOALKLTRIOLS CONTAINING CYCLIC SUBSTITUENTS, PROCESSES AND INTERMEDIATE PRODUCTS FOR THEIR PREPARATION AND THEIR USE AS ANTIVIRAL AND ANTIPARASITIC AGENTS

This application is a continuation of application Ser. No. 07/907,571 filed Jul. 2, 1992, now abandoned.

The present invention relates to cycloalkyltriol derivatives containing heterocyclic substituents, processes and intermediate products for the preparation of these compounds and their use as antiviral and antiparasitic agents.

In the compounds of the formulae I and II according to the invention, a heterocyclic system A which contains at least one nitrogen atom is bonded to C-1' of the cycloalkyl radical, in particular to C-1' of the cyclopentyl or cyclohexyl radical, via a nitrogen atom.

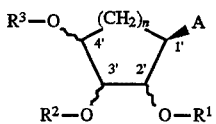

Formula I

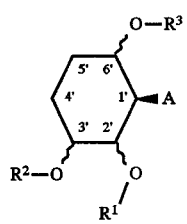

Formula II

The invention particularly relates to cyclopentane- and cyclohexanetriol derivatives of purines, pyrimidines, pyridines, pyridazines, imidazo-[4,5-d]-pyridazines, benzimidazoles, triazoles, imidazoles and imides.

The invention furthermore relates to the physiologically tolerated salts of the compounds mentioned with organic and inorganic acids, such as, for example, salts with acetic acid, lactic acid, malic acid, p-toluenesulfonic acid, methanesulfonic acid, isethionic acid or hydrochloric acid, and salts with organic or inorganic bases, such as, for example, triethylamine, pyridine, ammonia or sodium hydroxide solution.

The invention furthermore relates to prodrugs of the compounds mentioned, prodrugs in this connection meaning derivatives which are converted into the parent substances in vivo.

Such prodrugs can be, for example, esters, which can be hydrolyzed in vivo, of organic or inorganic acids, or alkyl, cycloalkyl or benzyl ethers which can be split back into the corresponding alcohols oxidatively in vivo. These esters or ethers can be on any C-2', C-3', C-4' or C-6' oxygen function of the compounds of the formulae I and II, independently of one another. Amino, hydroxyl and mercapto groups of the heterocyclic system A in the formulae I and II can furthermore be modified in this sense.

Carbocyclic nucleoside analogs, such as aristeromycin (formula A) and neoplanocin A (formula B), are naturally occurring compounds which have, inter alia, an antiviral action (see, for example, P. Herdewijn et al., J. Med. Chem. 1985, Vol. 28, 1385; and E. De Clercq, Antimicrob. Agents Chemother. 1985, Vol. 28, 84).

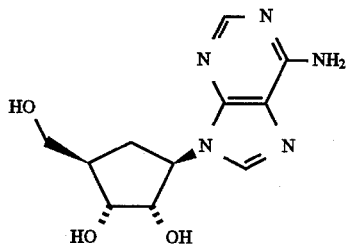

Formula A

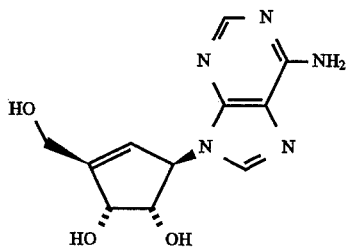

Formula B

Derivatives of these compounds in which the hydroxymethyl substituent in the 4'-position is replaced by hydrogen, alkyl or phenyl have an effect on the S-adenosyl-L-homocysteine/adenosine/homocysteine equilibrium by influencing the activity of S-adenosyl-L-homocysteine hydrolase, and proved to be antiviral active compounds (see, for example, M. Hasobe et al., Mol. Pharmacol.

On the other hand, compounds of the formula I in which A=adenin-9-yl or 8-aza-adenin-9-yl, $R^1$ and $R^2$=hydrogen and the substituent $OR^3$ is replaced by, for example, hydrogen or alkyl are described in a patent application (EPA 0368640) as being active against infections with parasites, such as Pneumocystis carinii or Trypanosoma brucei gambiense.

We have now found, surprisingly, that those cyclopentane- and cyclohexanetriol derivatives of the formulae I and II which contain heterocyclic substituents and in which the 4'-substituent is an optionally substituted hydroxyl function, and the physiologically tolerated salts thereof, have an antiviral or an antiparasitic action.

The invention accordingly relates to compounds of the formulae I and II

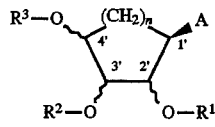

Formula I

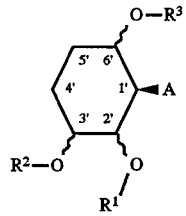

Formula II in which
A)
A is a mono- or bicyclic heterocyclic radical which is bonded to C-1' via nitrogen, contains at least one nitrogen atom and can be substituted, independently of one another, by up to three amino, hydroxyl, mercapto and/or halogen groups, it being possible for the amino, hydroxyl and/or mercapto groups to be substituted, independently of one another, by up to two radicals from the group comprising C1-C6-alkyl, C1-C6-acyl, benzyl, trityl, benzyloxymethyl and amidine groups and/or phenyl, which is in turn optionally substituted by halogen, C1-C6-alkyl, C1-C6-alkoxy, amino, C1-C6-alkylamino or C1-C12-dialkylamino, and it being possible for the NH functions of the heterocyclic radical to be substituted by C1-C6-acyl, benzyl or benzyloxymethyl groups, n is 1–4
and R¹, R² and R³ independently of one another are hydrogen, C1-C8-alkyl, C3-C8-alkenyl, C3-C8-alkynyl, C3-C8-cycloalkyl, C3-C8-cycloalkenyl, benzyl, trityl, benzyloxymethyl or C1-C8-acyl,
or R¹ and R² are part of a 1,3-dioxa-pentane ring, in the 2-position of which one or two hydrogen atoms can be substituted, independently of one another, by C1-C8-alkyl, C2-C16-dialkyl, C3-C8-cycloalkyl, C3-C8-cycloalkenyl, phenyl, diphenyl, C1-C8-alkoxy, C2-C16-dialkoxy, dimethylamino, oxygen or sulfur, or are part of a cyclic sulfite, cyclic sulfate, cyclic phosphite or cyclic phosphate, or the two hydrogen atoms are replaced by the group —CH₂—CH₂—CH₂—N(CH₃)—
and R³ is as described above, and physiologically tolerated salts thereof and obvious chemical equivalents, excluding the compound of the formula C.

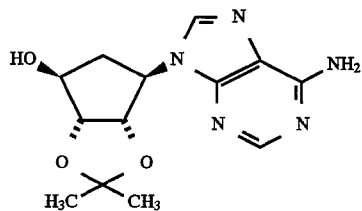

C

Using the notation system customary in nucleoside chemistry, the substituents A, OR¹, OR² and OR³ of the formulae I and II can independently of one another be in the alpha- or beta-position on the carbocyclic ring.

A preferred configuration is 1'β, 2'α, 3'α, 4β for the substituents A, OR¹, OR² and OR³ in compounds of the formula I, i.e. the substituents on C-1' and C-2' are trans relative to one another, those on C-2' and C-3' are cis relative to one another and those on C-3' and C-4' are trans relative to one another (formulae Ia) and 1'β, 2'α, 3'α, 6'β for the substituents A, OR¹, OR² and OR³ in compounds of the formula II, i.e. the substituents on C-1' and C-2' are trans relative to one another, those on C-2' and C-3' are cis relative to one another and those on C-6' and C-1' are cis relative to one another (formula IIa).

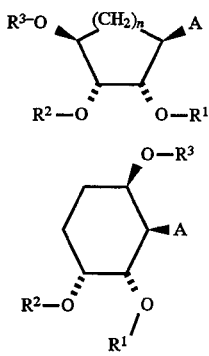

Formula Ia

Formula IIa

Particularly preferred compounds of the formulae Ia and IIa are those in which
B)
A is a purine, pyrimidine, 8-azapurine, 1-deazapurine, 3-deazapurine, benzimidazole, imidazo[4,5-d]pyridazine, pyridazine, pyridine, triazole, imidazole or imide which is bonded to C-1' via nitrogen and can be substituted, independently of one another, by up to three amino, hydroxyl, mercapto and/or halogen groups, it being possible for the amino, hydroxyl and/or mercapto groups to be substituted independently of one another by up to two radicals from the group comprising C1-C6-alkyl, C1-C6-acyl, benzyl, trityl, benzyloxymethyl and amidine groups and/or phenyl, which is in turn optionally substituted by halogen, C1-C6-alkyl, C1-C6-alkoxy, amino, C1-C6-alkylamino or C1-C12-dialkylamino, and it being possible for NH functions of the heterocyclic radical to be substituted by C1-C3-acyl, benzyl or benzyloxymethyl groups, n is 1–3
and R¹, R² and R³ independently of one another are hydrogen, C1-C5-alkyl, C3-C5-alkenyl, C3-C5-alkynyl, C3-C5-cycloalkyl, C3-C5-cycloalkenyl, benzyl, trityl, benzyloxymethyl or C1-C7-acyl,
or R¹ and R² are part of a 1,3-dioxa-pentane ring, in the 2-position of which one or two hydrogen atoms can be substituted, independently of one another, by C1-C8-alkyl, C2-C8-dialkyl, C3-C8-cycloalkyl, C3-C8-cycloalkenyl, phenyl, diphenyl, C1-C4-alkoxy, C2-C8-dialkoxy, dimethylamino, oxygen or sulfur, or are part of a cyclic sulfite, cyclic sulfate, cyclic phosphite or cyclic phosphate, or the two hydrogen atoms are replaced by the group —CH₂—CH₂—CH₂—N(CH₃)—
and R³ is as described above.

Compounds of the formulae Ia and IIa which are furthermore particularly preferred are those in which
C)
A is a purine, pyrimidine, 3-deazapurine, imidazo-[4,5-d]pyridazine, pyridazine, pyridine, imidazole or imide which is bonded to C-1' via nitrogen and can be substituted, independently of one another, by up to three amino, hydroxyl, mercapto and/or halogen groups, it being possible for the amino, hydroxyl and/or mercapto groups to be substituted independently of one another by up to two radicals from the group comprising C1-C3-alkyl, C1-C3-acyl, benzyl, trityl and amidine groups and/or phenyl, which is in turn optionally substituted by halogen, C1-C3-alkyl, C1-C3-alkoxy, amino, C1-C3-alkylamino or C1-C6-dialkylamino, n is 1 or 2
and R¹, R² and R³ independently of one another are hydrogen, C1-C3-alkyl, allyl, propargyl, cyclopentyl, benzyl, trityl, benzyloxymethyl or C1-C4-acyl,
or R¹ and R² are part of a 1,3-dioxa-pentane ring, in the 2-position of which one or two hydrogen atoms can be substituted, independently of one another, by C1-C3-alkyl, C2-C6-dialkyl, C4-C6-cycloalkyl, C4-C5-cycloalkenyl, phenyl, diphenyl, C1-C3-alkoxy, C2-C6-dialkoxy, oxygen or sulfur, or are part of a cyclic sulfite, cyclic sulfate, cyclic phosphite or cyclic phosphate,
and R³ is as described above.

Especially preferred compounds of the formulae Ia and IIa are those in which
D)
A is a purine, pyrimidine, 3-deazapurine, pyridazine or imidazole which is bonded to C-1' via nitrogen and is substituted, independently of one another, by up to three amino, hydroxyl, mercapto and/or halogen groups, it being possible for the amino, hydroxyl and/or mercapto groups to be substituted independently of one another by up to two radicals from the group comprising C1-C3-alkyl, C1-C3-acyl and benzyl groups and/or phenyl, which is in turn optionally substituted by chlorine, C1-C3-alkyl, C1-C3-alkoxy or amino, n is 2 and $R^1$, $R^2$ and $R^3$ independently of one another are hydrogen, C1-C3-alkyl, allyl, propargyl, cyclopentyl, benzyl, trityl, benzyloxymethyl or C1-C4-acyl, or $R^1$ and $R^2$ are part of a 1,3-dioxa-pentane ring, in the 2-position of which one or two hydrogen atoms can be substituted, independently of one another, by C1-C3-alkyl, cyclopentyl, phenyl, diphenyl, C1-C3-alkoxy, oxygen or sulfur, and $R^3$ is as described above.

The compounds of the formulae Ia and IIa in which A has the meanings given in the examples and $R^1$, $R^2$ and $R^3$ are H are of special importance.

Processes for the preparation of the carbocyclic nucleoside analogs of the type of the formulae A and B are described, for example, by V. E. Marquez, M. -I. Lim, Medicinal research Reviews Volume 6, 1-40 (1986).

Another path in which as the key step a palladium-catalyzed addition of epoxycyclopentenes onto adenine is used for the synthesis of aristeromycin (compound of the formula A), is described by B. M. Trost, G. -H. Kuo and T. Benneche, J. Am. Chem. Soc. Vol. 110, 621 (1988). This path is also taken for the synthesis of the adenin-9-yl, thymin-1-yl, cytosin-1-yl and 6-O-benzylguanin-9-yl derivatives of carbocyclic phosphonates in EPA 0 369 409, but without the cyclopentane- and cyclohexanetriol derivatives according to the invention thereby having been prepared or investigated for their antiviral or antiparasitic action. Only one derivative (compound of the formula Ia, in which A=adenin-9-yl, n=1 and $R^1$-$R^3$=hydrogen) is passed through in a synthesis sequence (B. M. Trost et al., J. Am. Chem. Soc. Volume 110, 621 (1988)), without isolation or direct characterization having taken place.

It has now been found that 1) a wide range of nitrogen-containing heterocyclic compounds having at least one NH function contained in the ring undergoes this palladium-catalyzed reaction with epoxycyclopentene and with 1,2-epoxy-cyclohex-3-ene to form the cis adduct of the formula III, in which $R^4$ is hydrogen,

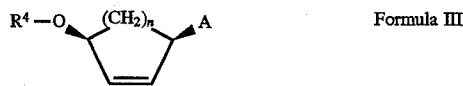

Formula III and that if 1,2-epoxy-cyclohex-3-ene is used, the 1,2-cis-adduct (compounds of the formula IV, in which $R^4$ is hydrogen) can be another reaction product;

Formula IV 2) the silylated, preferably trimethylsilylated, or acylated, preferably acetylated, derivatives of the nitrogen-containing heterocyclic compounds can advantageously be employed in this reaction to give compounds of the formulae III and IV, in which $R^4$ is trialkylsilyl, preferably trimethylsilyl, or acyl, preferably acetyl;

3) compounds of the formulae I and II, preferably compounds of the formulae Ia and IIa, can be prepared from the compounds of the formulae III and IV by cis-hydroxylation with, for example, osmium tetroxide/N-methylmorpholine N-oxide.

The invention thus furthermore relates to

E)

the preparation of compounds of the formulae III and IV, in which $R^4$ is hydrogen, trialkylsilyl, preferably trimethylsilyl, or acyl, preferably acetyl, and A is as defined above, which comprises reacting one equivalent of a nitrogen-containing heterocyclic compound which is defined as under A), preferably as under B), especially preferably as under C), having at least one free NH function or at least one silylated, preferably trimethylsilylated, or at least one acylated, preferably acetylated, N function in the heterocyclic radical, it being possible for further NH functions in, and amino, hydroxyl and mercapto functions on the heterocyclic radical to be substituted by trimethylsilyl, acyl, benzyl, benzyloxymethyl, dimethylaminomethylidene or N-methyl-2-pyrrolidinylidene, with 0.001–0.5 equivalent, preferably 0.005–0.1 equivalent, of a palladium(0) catalyst, such as tetrakis(triphenylphosphine)palladium(0) or tetrakis (triisopropyl phosphite)palladium(0), preferably tetrakis (triisopropyl phosphite)palladium(0), which can be prepared in situ from palladium(II) acetate, the particular phosphine or phosphite and butyllithium, and with 1 equivalent of a 1,2-epoxycycloalk-3-ene, preferably epoxycyclopentene or 1,2-epoxy-cyclohex-3-ene, in a solvent, such as tetrahydrofuran, toluene, dimethylsulfoxide, dimethylformamide or N-methylpyrrolid-2-one, or mixtures thereof, preferably in tetrahydrofuran, dimethylsulfoxide or dimethylformamide, or mixtures thereof, at 0° C.–110° C., preferably initially at room temperature and later at 80°–90° C., under an inert gas atmosphere, for example argon, for 2–24 hours, preferably for 2–10 hours, to give compounds of the above-mentioned formulae III and/or IV, in which $R^4$ is hydrogen if a nitrogen-containing heterocyclic compound having at least one non-modified NH function has been employed in the above reaction, or $R^4$ is trialkylsilyl, preferably trimethylsilyl, if a nitrogen-containing heterocyclic compound, the NH function of which was modified by trialkylsilyl, preferably trimethylsilyl, was employed in the above reaction, or $R^4$ is acyl, preferably acetyl, if a nitrogen-containing heterocyclic radical, the NH function of which was modified by acyl, preferably acetyl, was employed in the above reaction.

Compounds of the formulae III and IV in which $R^4$ is trialkylsilyl or acyl can be converted into compounds of the formulae III and IV in which $R^4$ is hydrogen by hydrolysis, alcoholysis, ammonolysis or aminolysis.

Compounds of the formulae III and IV in which any amino, hydroxyl and mercapto groups present are substituted on the heterocyclic radical A by trimethylsilyl, acyl, benzyl, benzyloxymethyl, dimethylaminomethylidene or N-methyl-2-pyrrolidinylidene groups can be converted into compounds of the formulae III and IV in which the amino, hydroxyl and mercapto groups are free by hydrolysis, alcoholysis, ammonolysis, aminolysis or hydrogenolysis.

The invention furthermore relates to a process

F)

for the preparation of compounds of the formulae I and II, preferably of compounds of the formulae Ia and IIa, which comprises reacting 1 equivalent of the compounds of the formulae V or VI

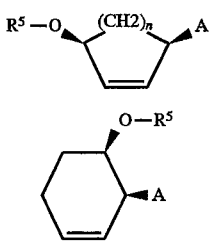

Formula V

Formula VI in which $R^5$ is $R^4$, alkyl, benzyl, trityl or benzyloxymethyl and A is a nitrogen-containing heterocyclic radical as defined in A), preferably as defined in B), especially preferably as defined in C), it being possible for any amino, hydroxyl and mercapto groups present on the heterocyclic radical and further NH groups in the heterocyclic radical to be substituted by trimethylsilyl, C1-C6-alkyl, C1-C6-acyl, benzyl, trityl, benzyloxymethyl, dimethylaminomethylidene or N-methyl-2-pyrrolidinylidene, with 1–5 equivalents, preferably 3 equivalents, of N-methyl-morpholine N-oxide and a catalytic amount of osmium tetroxide in tetrahydrofuran, acetone or water or mixtures thereof at 0°–60° C., preferably at room temperature, for 2 hours to 4 days, preferably for 1 to 3 days, compounds of the formulae VII and VIII, preferably compounds of the formulae VIIa and VIIIa, being formed.

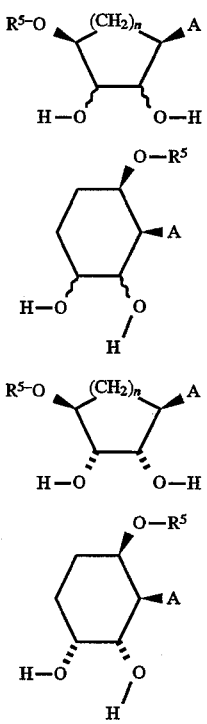

Formula VII

Formula VIII

Formula VIIa

Formula VIIIa

Compounds of the formulae VII and VIII, preferably compounds of the formulae VIIa and VIIIa, can in turn be converted into compounds of the formulae I and II, preferably into compounds of the formulae Ia and IIa, in which the substituents A, $R^1$, $R^2$ and $R^3$ have the above-mentioned meanings, by standard operations.

The present invention furthermore relates to the compounds of the abovementioned formulae III, IV, V, VI, VII, VIIa, VIII and VIIIa, in which $R^4$ is hydrogen, C1-C9-trialkylsilyl, preferably trimethylsilyl, or C1-C6-alkyl or C1-C6-acyl, preferably acetyl, and $R^5$ has the same meaning as $R^4$ or is C1-C6-, preferably C1-C3-alkyl, benzyl, trityl or benzyloxymethyl, and A is a nitrogen-containing heterocyclic radical as defined above under A), preferably as defined under B), especially preferably as defined under C), it being possible for any amino, hydroxyl and mercapto groups present on the heterocyclic radical and other NH groups in the heterocyclic radical to be substituted by trimethylsilyl, C1-C6-acyl, benzyl, trityl, benzyloxymethyl, dimethylaminomethylidene or N-methyl-2-pyrrolidinylidene, with the proviso that in compounds of the formulae III and V, $R^4$ and $R^5$ are not hydrogen if n is 1 and A is adenin-9-yl, thymin-1-yl, cytosin-1-yl, $N^4$-dimethylaminomethylidene-cytosin-1-yl, 6-benzyloxy-2-aminopurin-9-yl, 6-benzyloxy-2-monomethoxytritylaminopurin-9-yl or pyrimidin-2(1H)-on-1-yl, and that in compounds of the formula VIIa, $R^5$ is not hydrogen if n is 1 and A is adenin-9-yl.

The heterocyclic radicals of the abovementioned formulae I and II bonded as substituents A on C-1' can be, for example, purin-9-yl, purin-7-yl, 2-aminopurin-9-yl, 2-aminopurin-7-yl, 6-chloropurin-9-yl, 6-chloropurin-7-yl, 6-aminopurin-9-yl, 6-aminopurin-7-yl, 6-aminopurin-3-yl, hypoxanthin-9-yl, hypoxanthin-7-yl, 6-mercaptopurin-9-yl, 6-methylthiopurin-9-yl, 6-dimethylaminopurin-9-yl, 6-methylaminopurin-9-yl, 6-isopropoxypurin-9-yl, 2,6-dichloropurin-9-yl, 2-amino-6-chloro-purin-9-yl, 2,6-diaminopurin-9-yl, isoguanin-9-yl, guanin-9-yl, 2-amino-6-isopropoxypurin-9-yl, 8-bromoguanin-9-yl, 8-hydroxyguanin-9-yl, 8-aminoguanin-9-yl, 6-amino-1-deaza-purin-9-yl, uracil-1-yl, cytosin-1-yl, thymin-1-yl, 6-methylcytosin-1-yl, 5-methyl-4-(1,2,4-triazol-1-yl)-pyrimidin-1H-2-on-1-yl, 5-ethyluracil-1-yl, 5-isopropyluracil-1-yl, 5-E-(2-bromovinyl)-uracil-1-yl, 5-fluoro- or 5-chlorouracil-1-yl, 6-phenylthiothymin-1-yl, pyrimidin-2(1H) -on-1-yl, benzimidazol-1-yl, 1H-imidazo [4,5-d]pyridazin-4(5H) -on-1-yl, 5-methyl-1H-imidazo [4,5-d]pyridazin-4(5H)-on-1-yl, 4-amino-1H-imidazo [4,5-d]pyridazin-1-yl, 4-chloro-1H-imidazo [4,5-d]pyridazin-1-yl, pyridazin-3(2H)-on-2-yl, 4,5-disubstituted pyridazin-3 (2H) -on-2-yl, pyridine-2-on-1-yl, pyridin-4-on-1-yl, 1,2,4-triazol-1-yl, 3-carboxamido-1,2,4-triazol-1-yl, 5-amino-4 -carboxamido-imidazol-1-yl, phthalimido, succinimido or maleimido, which are unsubstituted, or in which amino, hydroxyl and mercapto groups on the heterocyclic radical and NH groups in the heterocyclic radical can be provided with acyl, benzyl or amidine functions.

The alkyl groups mentioned as substituents can be branched or unbranched.

Examples of alkyl groups are the methyl, ethyl, propyl, isopropyl, butyl, isobutyl or tert.-butyl group.

Examples of alkenyl groups are the 2-propen-1-yl, 3-buten-1-yl and the 3-methyl-2-buten-1-yl group.

Examples of alkynyl groups are the 2-propin-1-yl and the 2-butin-1-yl group.

Examples of cycloalkyl groups are the cyclobutyl, cyclopentyl and the cyclohexyl group.

Examples of cycloalkene groups are the cyclopentene, cyclohexene and cycloheptene group.

The acyl groups mentioned as substituents can be aliphatic, cycloaliphatic or aromatic.

Examples of acyl groups are the formyl, acetyl, propionyl, butyryl, isobutyryl, pivaloyl, valeroyl, cyclohexanoyl or benzoyl group.

The alkoxy groups mentioned as substituents can be, for example, the methoxy, ethoxy, propoxy or isopropoxy group.

The amidine functions mentioned as substituents can be acyclic or cyclic.

Examples of amidine functions are the dimethylaminomethylidene or the N-methyl-2-pyrrolidinylidene group.

The compounds of the formulae I, Ia, II and IIa according to the invention can contain one or more chiral centers. The compounds are as a rule in the form of racemates; preparation or isolation of the pure enantiomers is possible. The invention therefore relates both to the pure enantiomers and to mixtures thereof, such as, for example, the associated racemate.

The present invention furthermore relates to medicaments containing at least one compound according to the invention.

The medicaments according to the invention can be used enterally (orally), parenterally (intravenously), rectally or locally (topically). They can be administered in the form of solutions, powders (tablets, capsules, including microcapsules), ointments (creams or gel) or suppositories. Possible auxiliaries for such formulations are the pharmaceutically customary liquid or solid fillers and extenders, solvents, emulsifiers, lubricants, flavor correctants, dyestuffs and/or buffer substances. 0.1–10, preferably 0.2–8 mg/kg of body weight are administered as an advantageous dosage. The formulations are advantageously administered in dosage units which contain at least the effective daily amount of the compounds according to the invention, for example 30–300 mg, preferably 50–250 mg.

The compounds according to the invention can also be administered in combination with other antiviral or antiparasitic agents and immunostimulants, such as interferons.

The present invention is illustrated in more detail by the following embodiment examples and by the content of the patent claims.

EXAMPLES

1.1.1. and 1.1.2.

Compound of the formula III in which A is adenin-9-yl, n is 1 and $R^4$ is hydrogen (Example 1.1.1.) and compound of the formula III in which N is adenin-3-yl, n is 1 and $R^4$ is hydrogen (Example 1.1.2.):

a) Reaction of adenine with epoxycyclopentene:

89.8 mg (0.4 mmol) of palladium(II) acetate, 1 ml (4.0 mmol) of triisopropyl phosphite and 0.58 ml (0.8 mmol) of 1.4M n-BuLi in hexane are added to 30 ml of anhydrous tetrahydrofuran at 0° C. under an inert gas (argon). The mixture is stirred for 10 minutes, before 30 ml of anhydrous dimethylsulfoxide and 8.66 g (64 mmol) of adenine are added. The mixture is stirred for a further 15 minutes, before a solution of 5.7 g (69.5 mmol) of 1,2-epoxycyclopentene in 20 ml of anhydrous tetrahydrofuran is added dropwise over a period of 4–5 hours. The suspension is then stirred at 0° C. for a further 3 hours. After the ice-bath has been removed, the mixture is allowed to reach room temperature overnight. The brownish suspension is then added to 300 ml of ethanol and the mixture is stirred at room temperature for 30 minutes. The resulting suspension is filtered with suction and the residue is washed with ethanol and dried. The colorless residue consists of 2.75 g of adenine. The filtrate is concentrated and the residue is chromatographed over neutral aluminum oxide using methylene chloride/methanol 9/1. 2.66 g (28 % of theory, based on the adenine reacted) of 9-[(1RS,4SR)-4-hydroxy-cyclopent-2-en-1-yl]adenine (Example 1.1.1.) are obtained as the first fraction with a melting point of 176°–180° C. as colorless crystals.

1H NMR (270 MHz, $d_6$-DMSO), δ[ppm]: 8.14 (s, 1H), 8.07 (s, 1H), 7.20 (s, 2H), 6.19 (m, 1H), 5.98 (m, 1H), 5.51 (m, 1H), 5.44 (m, 1H), 4.72 (m, 1H), 2.89 (m, 1H), 1.74 (m, 1H); 13C NMR (67.93 MHz, $d_6$-DMSO), δ[ppm]: 156.01, 152.16, 148.83, 139.28, 139.24, 119.01, 73.74, 57.12, 41.10; UV-VIS [nm, log ¯]: (0.1N HCl): 259.5, 4.13; ($H_2O$, pH 6.0): 262.0, 4.18; (glycine/NaOH buffer, pH 11): 261.5, 4.20.

0.95 g (10% of theory, based on the adenine reacted) of 3-[(1RS,4SR)-4-hydroxy-cyclopent-2-en-1-yl]adenine (Example 1.1.2.) is obtained as the second fraction with a melting point of 270°–276° C. as colorless crystals. 1H NMR (270 MHz, $d_6$-DMSO), δ[ppm]: 8.31 (s, 1H), 7.93 (s, 2H), 7.74 (s, 1H), 6.63 (d, 1H), 6.25 (m, 1H), 5.97 (m, 1H), 5.61 (d, 1H), 4.70 (t, 1H), 2.92 (m, 1H), 1.92 (m, 1H); 13C NMR(67.93 MHz, $d_6$-DMSO), δ[ppm]: 159.86, 152.10, 151.24, 143.49, 139.94, 130.49, 110.56, 73.56, 60.15, 43.17; UV-VIS [nm, log ¯]: 0.1N HCl): 275, 4.25; ($H_2O$, pH 6.0): 274, 4.14; (glycine/NaOH buffer, pH 11): 273, 4.11.

b) Reaction of persilylated adenine with epoxycyclopentene:

The reaction (3 hours at 0° C., then overnight at room temperature) of 94.5 g (0.7 mol) of adenine which had been converted into the persilyl derivative by reaction with hexamethyldisilazane and 4 g of ammonium sulfate in xylene at the reflux temperature and had been dissolved in 600 ml of dry tetrahydrofuran, with palladium(0) catalyst (3.15 g (0.014 mol) of palladium(II) acetate, 38.1 ml (0.14 mol) of triisopropyl phosphite and 17.5 ml (0.028 mol) of a 1.6 molar solution of butyllithium in n-hexane) and a solution of 68 g of crude epoxycyclopentene in 350 ml of dry tetrahydrofuran under inert argon gas in 500 ml of dry tetrahydrofuran gave, after hydrolysis with methanol, in addition to 19.1 g of unreacted adenine, 76.7 g (63.3% of theory, based on the adenine reacted) of 9-[(1RS, 4SR)-4-hydroxy-cyclopent-2-en-1-yl]adenine (Example 1.1.1.) and 30.9 g (25.5% of theory, based on the adenine reacted) of 3-[(1RS, 4SR)-4-hydroxycyclopent-2-en-1-yl]adenine (Example 1.1.2.) after chromatography(silica gel, methylene chloride/ methanol 9/1).

c) Reaction of the compound from Example 1.5.1. with $NH_3$:

0.5 g (2.1 mmol) of the compound from Example 1.5.1. is dissolved in 25 ml of n-propanol. 50 ml of liquid $NH_3$ are added and the mixture is treated under a pressure of 50 bar of nitrogen at 100° C. in an autoclave for 10 hours. The reaction product is concentrated and the residue is chromatographed over silica gel using methylene chloride/ methanol 9:1. 0.38 g (83.4% of theory) of 9-[(1RS,4SR)-4-hydroxycyclopent-2-en-1-yl)adenine of melting point 180° C. is obtained.

1.2.

Compound of the formula III in which A is [$N^6$-(N-methyl-2-pyrrolidin-ylidene)]adenin-9-yl, n is 1 and $R^4$ is hydrogen:

a) Reaction of $N^6$-(N-methyl-2-pyrrolidin-ylidene)adenine with epoxycyclopentene:

224 mg (1 mmol) of palladium(II) acetate, 2.5 ml (10 mmol) of triisopropyl phosphite and 1.5 ml of 1.6 molar n-butyllithium solution in n-hexane (2 mmol) are brought together in 40 ml of dry tetrahydrofuran at 0° C. under inert nitrogen gas and the mixture is stirred. After addition of 30 ml of dry dimethylsulfoxide, 4.32 g (20 mmol) of $N^6$-(N-methyl-pyrrolidin-ylidene)adenine (prepared by reaction of adenine with the diethyl acetal of N-methyl-pyrrolid-2-one in 2-propanol; beige powder, melting point: 248°–251° C.) are added; a solution of 1.64 g (20 mmol) of epoxycyclopentene in 20 ml of dry tetrahydrofuran is then added dropwise in the course of one hour. The solution is stirred at room temperature for 12 hours and then concentrated and the residue is chromatographed over silica gel (methylene chloride/methanol 9/1). 1.62 g (27% of theory) of $N^6$-(N-methyl-2-pyrrolidin-ylidene)-9-[(1RS,4SR)-4-hydroxy-cyclopent-2-en-1-yl]adenine of melting point 135°–138° C.

are obtained in a regiospecific manner. 1H NMR (270 MHz, $d_6$-DMSO), δ[ppm]: 8.42 (s, 1H), 8.16 (s, 1H), 6.20 (m, 1H), 6.00 (m, 1H), 5.50 (m, 1H), 5.46 (d, 1H), 4.73 (m, 1H), 3.50 (t, 2H), 3.04 (s, 3H), 2.90 (m, 1H), 2.85 (t, 2H), 1.97 (p, 2H), 1.74 (m, 1H). $N^6$-(N-Methyl-2-pyrrolidin-ylidene)-9-(cyclopent-1-en-3-on-1-yl)adenine of melting point 200°–205° C. is isolated as a by-product (20 mg, 0.3% of theory). 1H NMR (270 MHz, CDCl$_3$), δ[ppm]: 8.64 (s, 1H), 8.13 (s, 1H), 7.19 (m, 1H), 3.53 (t, 2H), 3.34 (m, 2H), 3.20 (s, 3H), 3.07 (t, 2H), 2.65 (m, 2H), 2.10 (p, 2H).

b) Reaction of silylated $N^6$-(N-methyl-pyrrolidin-ylidene)-adenine with epoxycyclopentene:

If trimethylsilylated $N^6$-(N-methyl-pyrrolidin-yl-idene)adenine (prepared by reaction with N,O-bis-(trimethylsilyl)-acetamide) is employed in the above reaction, 29% of theory of $N^6$-(N-methyl-pyrrolidinylidene)-9-[(1RS,4SR)-4-hydroxy-cyclopent-2-en-1-yl]adenine are obtained in a regiospecific manner after reaction with tetrabutylammonium fluoride and after chromatography.

c) Reaction of 9-[(1RS,4SR)-4-hydroxy-cyclopent-2-en-1-yl]adenine with the diethyl acetal of N-methylpyrrolid-2-one:

The compound of Example 1.2. can also be obtained if 9-[(1RS,4SR)-4-hydroxy-cyclopent-2-en-1-yl]adenine is reacted with the diethyl acetal of N-methylpyrrolid-2-one in methylene chloride. Yield after chromatography on silica gel using methylene chloride/methanol 9/1: 98% of theory.

1.3.

Compound of the formula III in which N is adenin-9-yl $N^1$-oxide, n is 1 and $R^4$ is hydrogen (as the m-chlorobenzoic acid salt):

0.9 g (4.15 mmol) of the compound from Example 1.1.1. is stirred with 0.84 g (4.15 mmol) of 85% strength m-chloroperbenzoic acid in 50 ml of methylene chloride at room temperature for 2 days. The precipitate is filtered off with suction, stirred with 50 ml of diethyl ether and filtered off with suction again. The solid residue is dissolved in 2N HCl and the acid aqueous solution is extracted several times by shaking with diethyl ether and finally concentrated completely. The residue is extracted with hot ethanol in several portions. The ethanol extracts are concentrated and the residue is dried. 0.44 g (45.5% of theory) of the m-chlorobenzoic acid salt of the $N^1$-oxide of 9-[(1RS,4SR)-4-hydroxy-cyclo-pent-2-en-1-yl]adenine of melting point 198°–200° C. is obtained. 1H NMR (270 MHz, $d_6$-DMSO), δ[ppm]: 8.66 (s, 1H), 8.27 (s, broad, 1H), 8.22 (s, 1H), 7.89 (m, 2H), 7.70 (m, 1H), 7.53 (m, 1H), 6.20 (m, 1H), 6.04 (m, 1H), 5.45 (m, 1H), 5.28 (s, 1H), 4.72 (m, 1H), 2.91 (m, 1H), 1.73 (m, 1H).

1.4.

Compound of the formula III in which A is hypoxanthin-9-yl, n is 1 and $R^4$ is hydrogen:

6.51 g (30 mmol) of the adenine derivative from Example 1.1.1. are dissolved with 15.3 g (180 mmol) of sodium nitrite in a mixture of 150 ml of water, 15 ml of glacial acetic acid and 30 ml of 1N hydrochloric acid and the solution is stirred at room temperature for 2 days. The resulting suspension is concentrated to about ⅓ of the original volume and the precipitate is filtered off with suction and recrystallized from ethanol/water 2/1. 5.02 g (76.8% of theory) of 9-[(1RS, 4SR)-4-hydroxy-cyclopent-2-en-1-yl]hypoxanthine of melting point 274°–276° C. (decomposition) are obtained. 1H NMR (270 MHz), $d_6$-DMSO), δ[ppm]: 12.29 (s, 1H), 8.06 (s, 1H), 8.00 (s, 1H), 6.18 (m, 1H), 6.00 (m, 1H), 5.43 (m, 1H), 5.28 (d, 1H), 4.72 (m, 1H), 2.70 (m, 1H), 1.70 (m, 1H).

1.5.1. and 1.5.2.

Compounds of the formula III in which A is 6-chloropurin-9-yl (Example 1.5.1.) or 6-chloropurin-7-yl (Example 1.5.2.), n is 1 and $R^4$ is hydrogen:

Trimethylsilylated 6-chloropurine (prepared from 50 g (0.32 mol) of 6-chloropurine) is stirred with 5 mol % of the palladium(0) catalyst described above and an equivalent amount of epoxycyclopentene in tetrahydrofuran at room temperature for 24 hours. The reaction solution is heated with methanol for 1.5 hours, the precipitate formed is filtered off with suction, the resulting solution is concentrated and the residue is chromatographed over silica gel using methylene chloride/methanol 20/1. 18.9 g (25% of theory) of 6-chloro-9-[(1RS,4SR)-4-hydroxy-cyclopent-2-en-1-yl]purine (Example 1.5.1.) are obtained as yellowish crystals of melting point 118° C. 1H-NMR (270 MHz, $d_6$-DMSO), δ[ppm]: 8.80 (s, 1H), 8.62 (s, 1H), 6.25 (m, 1H), 6.08 (m, 1H), 5.60 (m, 1H), 5.31 (d, 1H), 4.76 (m, 1H), 2.95 (m, 1H), 1.81 (m, 1H).

In a second fraction, 34.2 g (45.2% of theory) of 6-chloro-7-[(1RS,4SR)-4-hydroxy-cyclopent-2-en-1-yl]-purine (Example 1.5.2.) are obtained as yellow crystals of melting point 177° C. 1H NMR (270 MHz, $d_6$-DMSO), δ[ppm]: 8.81 (s, 1H), 8.68 (s, 1H), 6.30 (m, 1H), 6.18 (m, 1H), 5.84 (m, 1H), 5.27 (d, 1H), 4.75 (m, 1H), 2.99 (m, 1H), 1.73 (m, 1H).

The compound of Example 1.5.1. can be obtained in regioisomerically pure form (i.e. without contamination by the $N^7$-isomer) if 6-chloropurine is stirred with 5 mol % of the palladium(0) catalyst described above and with an equivalent amount of epoxycyclopentene in tetrahydrofuran at room temperature for 2 days. The crude product thus obtained is dissolved in 2N sodium hydroxide solution, the solution is extracted several times by shaking with ethyl acetate, the organic phase is dried over sodium sulfate and concentrated and the residue is chromatographed over silica gel using methylene chloride/methanol 20/1. 6-Chloro-9-[(1RS,4SR)-4-hydroxy-cyclopent-2-en-1-yl]purine is obtained in this manner in a yield of 74%.

1.6.

Compound of the formula III in which A is adenin-7-yl, n is 1 and $R^4$ is hydrogen:

0.5 g (2.1 mmol) of the compound of Example 1.5.2. are dissolved in 30 ml of n-pentanol saturated with ammonia gas and the solution is stirred under a pressure of 50 bar at 100° C. in an autoclave for 10 hours. The crude product is concentrated to dryness and chromatographed on silica gel using methylene chloride/methanol 7/3 to give 0.32 g (70.2% of theory) of 7-[(1RS,4SR)-4-hydroxy-cyclopent-2-en-1-yl]adenine as colorless crystals of melting point 195°–197° C. 1H-NMR (270 MHz, $d_6$-DMSO), δ[ppm]: 8.19 (center of two incompletely resolved singlets, 2H), 6.93 (s, 2H), 6.22 (m, 1H), 6.13 (m, 1H), 5.68 (m, 1H), 5.38 (d, 1H), 4.72 (m, 1H), 2.98 (m, 1H), 1.52 (m, 1H). 13C NMR (67.93 MHz, $d_6$-DMSO), δ[ppm]: 159.86, 152.10, 151.24, 143.49, 139.94, 130.49, 110.56, 73.56, 60.15, 43.17.

1.7.

Compound of the formula III in which N is 6-(2,2-diphenylethylamino)-purin-9-yl, n is 1 and $R^4$ is hydrogen:

4.52 g (0.02 mol) of the compound from Example 1.5.1. are heated under reflux with 5.91 g (0.03 mol) of 2,2-diphenylethylamine and 3.03 g (0.03 mol) of triethylamine in 150 ml of ethanol for 6 hours. The reaction solution is concentrated, the residue is dissolved in 200 ml of dichloroethane, the solution is extracted several times by shaking with water, the organic phase is dried over sodium sulfate and concentrated and the residue is chromatographed over silica gel using methylene chloride/methanol 9/1. 6 g (75.7% of theory) of 6-(2,2-diphenylethylamino)-9-[(1RS,4SR)-4-hydroxy-cyclopent-2-en-1-yl]purine are obtained as pale brown crystals of melting point 165°–169° C. (after crystallisation from 2-propanol/n-hexane 1/1). 1H NMR (270 MHz, $d_6$-DMSO), δ[ppm]: 8.28 (s, 1H), 8.03 (s, 1H), 7.72 (s, 1H), 7.38–7.14 (m, 10H), 6.18 (m, 1H), 5.96 (m, 1H), 5.51 (d, 1H), 5.44 (m, 1H), 4.71 (m, 1H), 4.60 (t, 1H), 4.13 (m, 2H), 2.89 (m, 1H), 1.74 (m, 1H).

1.8.

Compound of the formula III in which N is 2-amino-6-chloro-purin-9-yl, n is 1 and $R^4$ is hydrogen:

39.9 g (0.235 mol) of 2-amino-6-chloropurine are stirred in a mixture of 100 ml of tetrahydrofuran and 100 ml of dimethylsulfoxide with 5 mol % of the catalyst described above and with an equivalent amount of epoxycyclopentene at room temperature for 90 hours. The resulting suspension is filtered (1.7 g of 2-amino-6-chloropurine); the filtrate is concentrated and the residue is chromatographed over silica gel using dichloroethane/methanol 9/1. In addition to a further 3.2 g of 2-amino-6-chloropurine, 48.5 g (93.4% of theory, based on the 2-amino-6-chloropurine reacted) of 2-amino-6-chloro-9-[(1RS,4SR)-4-hydroxy-cyclopent-2-en-1-yl)purine are obtained as a yellow oil. The oil crystallizes after some time, and the substance then has a melting point of 148° to 151° C. 1H NMR (270 MHz, $d_6$-DMSO), δ[ppm]: 8.04 (s, 1H), 6.91 (s, 2H), 6.20 (m, 1H), 6.00 (m, 1H), 5.32 (m, 1H), 5.25 (d, 1H), 2.86 (m, 1H), 1.68 (m, 1H).

1.9.

Compound of the formula III in which A is 2,6-diaminopurin-9-yl, n is 1 and $R^4$ is hydrogen:

6.0 g (23.8 mmol) of the compound of Example 1.8. are suspended in 80 ml of formamide, and the mixture is heated to 100° C. Gaseous ammonia is passed through the resulting solution for 7 hours. The reaction solution is cooled and acidified with 60 ml of a saturated solution of hydrochloric acid gas in methanol, and 800 ml of acetone are added. The precipitate is filtered off with suction and dissolved in 200 ml of water, 50 ml of 2N ammonia solution are added and the mixture is concentrated to dryness. The residue is extracted several times with hot acetone; the acetone extracts are filtered and the filtrate is concentrated to dryness. The residue is stirred with diethyl ether, filtered off with suction and dried. 3.91 g (70.8% of theory) of 2,6-diamino-9-[(1RS,4SR)-4-hydroxy-cyclopent-2-en-1-yl]purine of melting point 167°–170° C. are obtained. 1H NMR (60 MHz, $d_6$-DMSO), δ[ppm]: 7.70 (s, 1H), 7.03 (s, 2H), 6.12 (m, 5H), 5.30 (m, 1H), 4.73 (m, 1H), 2.88 (m, 1H), 1.68 (m, 1H).

1.10.

Compound of the formula III in which A is 2-amino-6-mercapto-purin-9-yl, n is 1 and $R^4$ is hydrogen:

6.0 g (23.8 mmol) of the compound from Example 1.8. are suspended with 2.0 g (26.2 mmol) of thiourea in 80 ml of 2-propanol, and the suspension is stirred and heated under reflux for 45 minutes. The resulting suspension is filtered; active charcoal is added to the residue in 30 ml of hot water, the mixture is filtered and the product is cooled. 2.76 g of 2-amino-6-mercapto-9-[(1RS,4SR)-4-hydroxy-cyclo-pent-2-en-1-yl]purine of melting point >250° C. crystallize. Chromatography of the concentrated mother liquors over silica gel using methylene chloride/methanol 9/1 gives a further 1.03 g of product, so that the total yield is 63.9% of theory. 1H NMR (60 MHz, $d_6$-DMSO), δ[ppm]: 12.5 (s, 1H), 8.45 (s, 1H), 7.20 (s, 2H), 6.15 (m, 2H), 5.83–5.12 (m, 2H), 4.75 (m, 1H), 2.85 (m, 1H), 1.73 (m, 1H).

1.11.

Compound of the formula III in which N is 2-aminopurin-9-yl, n is 1 and $R^4$ is hydrogen:

a) 3.74 g (15 mmol) of the compound of Example 1.10. are suspended in 600 ml of dry ethanol, 15 g of Raney nickel are added and the mixture is stirred at the reflux temperature for 2 hours. The cooled suspension is filtered, the residue is washed with hot ethanol, the combined ethanol solutions are concentrated and the residue is stirred with diethyl ether/acetone 10/1 and filtered off. The residue is washed with diethyl ether and dried. 1.34 g (41.2% of theory) of 2-amino-9-[(1RS,4SR)-4-hydroxy-cyclopent-2-en-1-yl]purine of melting point 144°–147° C. are obtained. 1H NMR (60 MHz, $d_6$-DMSO), δ[ppm]: 8.67 (s, 1H), 8.05 (s, 1H), 6.53 (s, 2H), 6.13 (m, 2H), 5.58–5.20 (m, 2H), 4.77 (m, 1H), 2.92 (m, 1H), 1.70 (m, 1H).

b) 3.74 g (15 mmol) of the compound of Example 1.8. and 7 g of zinc powder are suspended in 150 ml of water. The suspension is heated to the reflux temperature, and 2 ml of concentrated aqueous ammonia solution are added dropwise over a period of 2 hours, while stirring. The cooled suspension is filtered, the residue on the filter is washed with methanol, the filtrate is concentrated and the residue is chromatographed over silica gel using methylene chloride/methanol 5/1. 2.66 g (81.7% of theory) of 2-amino-9-[(1RS, 4SR)-4-hydroxy-cyclopent-2-en-1-yl]purine of melting point 147°–149° C. are obtained. 0.22 g (6.3% of theory) of the diaminopurine compound of Example 1.9. is isolated as a by-product.

1.12.1. and 1.12.2.

Compounds of the formula III in which A is guanin-9-yl, n is 1 and $R^4$ is hydrogen (Example 1.12.1.) and in which A is guanin-7-yl, n is 1 and $R^4$ is hydrogen (Example 1.12.2.):

a) 105.8 g (0.7 mol) of guanine are reacted in 600 ml of dry xylene with 500 ml of hexamethyldisilazane and 4 g of ammonium sulfate for 2 days to give the pertrimethylsilyl compound. The oily silylguanine compound is dissolved in 400 ml of dry tetrahydrofuran and the solution is added dropwise to a solution of the palladium(0) catalyst (5 mol %) prepared in situ as described above in 450 ml of tetrahydrofuran at 0° C. A solution of the equivalent amount of epoxycyclopentene in 200 ml of tetrahydrofuran is then added dropwise over a period of 2–3 hours. The resulting solution is stirred at room temperature for 3 days. 400 ml of methanol are added and the mixture is heated under reflux for 1 hour. During this operation, a very voluminous precipitate is formed, and can be converted into a homogeneous suspension after further stirring. The suspension thus obtained is filtered. 4.7 g of a mixture of the compounds 1.12.1. and 1.12.2. crystallize out of the filtrate. The residue on the filter is stirred with 1.2 l of water and filtered off with suction again. This residue on the filter is washed with ethanol and then boiled up in several portions with 1 l of ethanol. On cooling, this ethanolic solution gives 4.75 g of 9-[(1RS,4SR)-4-hydroxy-cyclopent-2-en-1-yl]guanine as beige crystals of melting point 265°–273° C. (decomposition) (compound of Example 1.12.1.). 1H NMR (270 MHz, d6-DMSO), δ[ppm]: 10.56 (s, 1H), 7.60 (s, 1H), 6.42 (s, 2H), 6.15 (m, 1H), 5.95 (m, 1H), 5.24 (d, 1H), 5.20 (m, 1H), 4.70 (m, 1H), 2.82 (m, 1H), 1.60 (m, 1H). If the residue on the filter is boiled up again with 1.5 l of water, 5.0 g of 7-[(1RS,4SR)-4-hydroxy-cyclopent-2-en-1-yl]guanine of melting point >310° C. crystallize out of the aqueous filtrate (compound of Example 1.12.2.). 1H NMR (270 MHz, d6-DMSO), δ[ppm]: 10.80 (s, 1H), 7.84 (s, 1H), 6.15 (m, 1H), 6.13 (s, 2H), 6.01 (m, 1H), 5.61 (m, 1H), 5.18 (d, 1H), 4.68 (m, 1H), 2.88 (m, 1H), 1.60 (m, 1H). The residue which remains on the filter of 82.7 g consists of a mixture of the compounds of Example 1.12.1. and 1.12.2.

b) 2 g (7.9 mmol) of the compound of Example 1.8. are suspended in 50 ml of 2A aqueous hydrochloric acid and the suspension is heated to about 70° C. for 6 hours, while stirring. Ice is added to the resulting yellow suspension and the pH is carefully brought to 7–8 by addition of solid sodium carbonate in portions. The precipitate is filtered off with suction, washed with a little cold water and dried. 1.3 g (70.2% of theory) of 9-[(1RS,4SR)-4-hydroxy-cyclopent-2-en-1-yl]guanine (compound of Example 1.12.1.) of melting point 270°–273° C. are obtained.

c) 19.3 g (0.1 mol) of $N^2$-acetylguanine are reacted with hexamethyldisilazane and a catalytic amount of ammonium sulfate in xylene to give the corresponding pertrimethylsilylated compound. This is reacted in tetrahydrofuran with 5 mol % of the palladium(0) catalyst prepared in situ as described above and an equivalent Mount of epoxycyclopentene at room temperature for 16 hours. Methanol and water are added and the mixture is heated under reflux for 3 hours. The mixture is concentrated to dryness, the residue is dissolved in 2N potassium carbonate and the mixture is extracted by shaking with ethyl acetate. The aqueous phase is neutralized with acetic acid and concentrated to dryness and the residue is acetylated with acetic anhydride and catalytic amounts of N,N-dimethylaminopyridine in methylene chloride. The reaction product is chromatographed over silica gel using methylene chloride/methanol 20/1. 7.42 g (27% of theory) of $N^2$-acetyl-7-[(1RS,4SR)-4-acetoxy-cyclopent-2-en-1-yl]guanine (N,O-diacetyl compound of Example 1.12.2.) of melting point 219°–220° C. (decomposition) are obtained.

1H NMR (270 MHz, d6-DMSO), δ[ppm]: 12.12 (s, 1H), 11.59 (s, 1H), 8.03 (s, 1H), 6.34 (m, 1H), 6.27 (m, 1H), 5.78 (m, 1H), 5.60 (m, 1H), 3.04 (m, 1H), 2.18 (s, 3H), 2.01 (s, 3H), 1.87 (m, 1H). This compound is treated in methanol with 40% strength aqueous methylamine solution at the reflux temperature and gives 5.3 g (97.2% of theory) of 7-[(1RS,4SR)-4-hydroxy-cyclopent-2-en-1-yl]guanine (compound of Example 1.12.2.) of melting point >310° C.

1.13.

Compound of the formula III in which A is $N^2$-acetyl-6-O-diphenylcarbamoyl-guanin-7-yl, n is 1 and $R^4$ is hydrogen:

0.15 mol of epoxycyclopentene is added to 38.8 g (0.1 mol) of $N^2$-acetyl-6-O-diphenylcarbamoyl-guanine (prepared by the method of R. Zou and M. J. Robins: Can. J. Chem. Volume 65, 1436 (1987)) with 5 mol % of the palladium(0) catalyst prepared in situ as described above in a mixture of 200 ml of dry tetrahydrofuran and 200 ml of dry dimethylsulfoxide at 0° C., and the mixture is stirred at room temperature for 15 hours, with exclusion of atmospheric oxygen. The resulting suspension is concentrated, 300 ml of methanol are added and the mixture is stirred at room temperature for 2 hours and filtered with suction. The filtrate is freed from the solvent and the oily residue is chromatographed over silica gel using methylene chloride/methanol 20/1. In addition to 5.4 g of diphenylamine, 5.67 g (12.7% of theory) of $N^2$-acetyl-6-O-diphenylcarbamoyl-7-[(1RS,4SR)- 4-hydroxy-cyclopent-2-en-1-yl]guanine of melting point 146°–149° C. are obtained. 1H NMR (270 MHz, d6-DMSO), δ[ppm]: 10.70 (s, 1H), 8.38 (s, 1H), 7.53–7.41 (m, 8H), 7.37–7.29 (m, 2H), 6.21 (m, 1H), 6.03 (m, 1H), 5.47 (m, 1H), 5.21 (d, 1H), 4.74 (m, 1H), 2.93 (m, 1H), 2.21 (s, 3H), 1.80 (m, 1H).

1.14.

Compound of the formula III in which A is $N^2$-acetylguanin-7-yl, n is 1 and $R^4$ is acetoxy:

0.5 g of ammonium sulfate and 125 ml of xylene are added to 58.2 g (0.15 mol) of $N^2$-acetyl-6-O-diphenylcarbamoyl-guanine in 125 ml of hexamethyldisilazane, and the mixture is heated under reflux for 3 hours. The resulting trimethylsilyl compound is dissolved with 5 mol % of the palladium(0) catalyst prepared in situ as described above in 300 ml of dry tetrahydrofuran, the equivalent Mount of epoxycyclopentene is added dropwise and the mixture is stirred at room temperature for 3 days. The resulting solution is concentrated, the residue is dissolved in methylene chloride, catalytic amounts of N,N-dimethylaminopyridine and an excess of acetic anhydride are added and the mixture is heated under reflux for 2 hours. The reaction product is freed from the solvent and chromatographed over silica gel using methylene chloride/methanol 20/1. In addition to 16.6 g of diphenylamine, 4.05 g (8.5% of theory) of $N^2$-acetyl-7-[(1RS,4SR)-4-acetoxy-cyclopent-2-en-1-yl]guanine of melting point 218°–222° C. are obtained. The 1H NMR spectrum of this compound agrees with that of the N,O-diacetyl compound in the description of Example 1.12.2., Method c).

13C NMR (67.93 MHz, d6-DMSO), δ[ppm]: 173.28, 169.91, 157.14, 152.64, 146.88, 141.34, 134.82, 134.04, 111.16, 76.80, 59.74, 38.88, 23.45, 20.73.

1.15.

Compound of the formula III in which A is 5-benzyloxymethyl-1H-imidazo[4,5-d]pyridazin-4(5H)-on-1-yl, n is 1 and $R^4$ is hydrogen:

The equivalent amount of epoxycyclopentene (dissolved in 45 ml of dry tetrahydrofuran) is slowly added as described above to 25.6 g of 5-benzyloxymethyl-1H-imidazo[4,5-d]pyridazin-4(5H)-one (0.1 mol) in 140 ml of dry tetrahydrofuran with 5 mol % of the palladium(0) catalyst prepared in situ, at 0° C., and the mixture is then stirred at room temperature for 10 hours. The resulting reaction solution is concentrated and the residue is chromatographed over neutral aluminum oxide using methylene chloride/methanol 20/1. 17.0 g (50.3% of theory) of 1-[(1RS,4SR)-4-hydroxy-cyclopent-2-en-1-yl]-5-benzyl-oxymethyl-1H-imidazo[4,5-d]pyridazin-4(5H)-one of melting point 122°–123° C. are obtained. 1H NMR (270 MHz, d6-DMSO), δ[ppm]: 8.48 (s, 1H), 8.36 (s, 1H), 7.32 (m, 5H), 6.22 (m, 1H), 6.08 (m, 1H), 6.00 (m, 1H), 5.59 (m, 2H), 5.26 (d, 1H), 4.73 (m, 1H), 4.69 (s, 2H), 2.97 (m, 1H), 1.69 (m, 1H).

1.16.

Compound of the formula III in which A is cytosin-1-yl, n is 1 and $R^4$ is hydrogen:

a) 52.5 g (0.47 mol) of cytosine are reacted with 38.5 g (0.47 mol) of epoxycyclopentene at 0° C., by slow addition, in a mixture of in each case 220 ml of dry tetrahydrofuran and dimethylsulfoxide with 1 mol % of the palladium(0)

catalyst prepared in situ as described above under an inert argon atmosphere. The reaction mixture is stirred at room temperature for 90 hours and then freed from the solvent and the residue is chromatographed over silica gel using methylene chloride/methanol 7/3. 71.8 g (79.2% of theory) of 1-[(1RS,4SR)-4-hydroxycyclopent-2-en-1-yl]cytosine of melting point 241°–242° C. are obtained. 1H-NMR (270 MHz, $d_6$-DMSO), δ[ppm]: 7.42 (d, 1H), 7.02 (s, 2H), 6.09 (m, 1H), 5.75 (m, 1H), 5.72 (d, 1H), 5.44 (m, 1H), 5.18 (d, 1H), 4.63 (m, 1H), 2.72 (m, 1H), 1.27 (m, 1H).

b) If trimethylsilylated cytosine is employed in this reaction, 85.3% of theory of the compound described under 1.16.a. are isolated after alcoholysis of the silylated allyl alcohol formed.

1.17.

Compound of the formula III in which A is uracil-1-yl, n is 1 and $R^4$ is hydrogen: a) 5.79 g (0.03 mol) of the compound of Example 1.16. are dissolved in 15.3 g (0.18 mol) of sodium nitrite in a mixture of 150 ml of water, 15 ml of glacial acetic acid and 30 ml of 1N hydrochloric acid, and the solution is stirred at room temperature for 2 days. The reaction mixture is concentrated, the residue is boiled up several times with acetone, the acetone extracts are concentrated and the residue is chromatographed over silica gel using methylene chloride/methanol 9/1. 3.65 g (62.7% of theory) of 1-[(1RS,4SR)-4-hydroxy-cyclopent-2-en-1-yl]uracil are obtained as a white powder of melting point 163°–164° C. 1H NMR (270 MHz, $d_6$-DMSO), δ[ppm]: 11.23 (s, 1H), 7.45 (d, 1H), 6.13 (m, 1H), 5.79 (m, 1H), 5.64 (d, 1H), 5.39 (m, 1H), 5.24 (d, 1H), 4.63 (m, 1H), 2.73 (m, 1H), 1.36 (m, 1H).

b) If uracil (21.5 g (0.192 mol)) is reacted with the equivalent amount of epoxycyclopentene in the customary manner in tetrahydrofuran/dimethylsulfoxide with 1 mol % of the palladium(0) catalyst described above, after chromatography using methylene chloride/methanol 9/1 on aluminum oxide, in addition to the $N^1,N^3$-bis-adduct (1,3-bis-[(1RS,4SR)-4-hydroxy-cyclopent-2-en-1-yl]uracil, diastereomer mixture, 21 g (39.6% of theory); 1H NMR (270 MHz, $d_6$-DMSO), δ[ppm]: 7.47 (d, 1H), 6.16 (m, 1H), 5.81 (m, 1H), 5.79 (s, 2H), 5.76 (m, 1H), 5.63 (t, 1H), 5.41 (m, 1H), 5.26 (d, 1H), 4.76 (d, 1H), 4.61 (m, 1H), 2.74 (m, 1H), 2.50 (m, 1H), 1.94 (m, 1H), 1.38 (m, 1H), which is obtained as an oil, 0.3 g (0.8% of theory) of the $N^1$-monoadduct (compound of Example 1.17.) of melting point 160°–162° C. is isolated.

1.18.1. and 1.18.2.

Compounds of the formula III in which A is 5-methyl-4-(1,2,4-triazol-1-yl)pyrimidin-2(1H)-on-1-yl, n is 1 and $R^4$ is hydrogen (Example 1.18.1.) and A is 5-methyl-4-methoxy-pyrimidin-2(1H)-on-1-yl, n is 1 and $R^4$ is hydrogen (Example 1.18.2.):

The equivalent amount of epoxycyclopentene is slowly added at 0° C. to 3.54 g (0.020 mol) of 5-methyl-4-(1,2,4-triazol-1-yl)pyrimidin-2(1H)-one (prepared by reaction of thymine with 1,2,4-triazole/POCl$_3$/triethylamine) in a mixture of 40 ml of dry tetrahydrofuran and 20 ml of dry dimethylsulfoxide with 5 mol % of the palladium(0) catalyst prepared in situ as above, and the reaction mixture is stirred at room temperature for 12 hours. The resulting suspension is filtered, the filtrate is concentrated and the residue is chromatographed over silica gel using methylene chloride/methanol 9/1. 1.34 g (25.8% of theory) of 1-[(1RS,4SR)-4-hydroxy-cyclopent-2-en-1-yl]-5-methyl-4-(1,2,4-triazol-1-yl)-pyrimidin-2(1H)-one (Example 1.18.1.) of melting point 198° to 204° C. are obtained. 1H NMR (270 KHz, $d_6$-DMSO), δ[ppm]: 9.31 (s, 1H), 8.38 (s, 1H), 8.07 (s, 1H), 6.25 (m, 1H), 5.92 (m, 1H), 5.52 (m, 1H), 5.28 (d, 1H), 4.71 (m, 1H), 2.87 (m, 1H), 2.30 (s, 3H), 1.47 (m, 1H).

0.59 g (13.2% of theory) of 1-[(1RS,4SR)-4-hydroxycyclopent-2-en-1-yl]-5-methyl-4-methoxy-pyrimidin-2(1H)-one (Example 1.18.2.) of melting point 143°–146° C. is isolated as a further product.

1H NMR (270 KHz, $d_6$-DMSO), δ[ppm]: 7.58 (s, 1H), 6.16 (m, 1H), 5.81 (m, 1H), 5.48 (m, 1H), 5.21 (s, 1H), 4.56 (m, 1H), 3.86 (s, 3H), 2.79 (m, 1H), 1.89 (s, 3H), 1.33 (m, 1H).

1.19.

Compound of the formula III in which A is 4-amino-5-methyl-pyrimidin-2(1H)-on-1-yl, n is 1 and $R^4$ is hydrogen:

a) 0.4 g (1.54 mmol) of the compound from Example 1.18.1. is suspended in concentrated aqueous ammonia and the suspension is stirred at room temperature for 12 hours. The reaction solution is concentrated to dryness and the residue is chromatographed over silica gel using methylene chloride/methanol 5/1. 73 mg (22.9% of theory) of the compound of Example 1.20. of melting point 190°–192° C. are obtained. 242 mg (75.9% of theory) of 4-amino-5-methyl-1-[(1RS,4SR)-4-hydroxy-cyclopent-2-en-1-yl]-pyrimidin-2(1H)-one of melting point 242°–245° C. are isolated as a second fraction.

b) 50 g (0.4 mol) of 5-methylcytosine are added to a solution of the palladium(0) catalyst (1.6 mol %) prepared in situ as described above in 200 ml of dry tetrahydrofuran/200 ml of dry dimethylsulfoxide at 5° C. 49.2 g (0.6 mol) of epoxycyclopentene, dissolved in 100 ml of tetrahydrofuran, are added dropwise to this suspension, while stirring (1.5 hours). The mixture is stirred at room temperature for 3 days and then concentrated, and the residue is stirred with 2N sodium carbonate solution, filtered off and washed with water and acetone. 20.2 g (24.4% of theory) of 4-amino-5-methyl-1-[(1RS,4SR)-4-hydroxy-cyclopent-2-en-1-yl]pyrimidin-2(1H)-one of melting point 241°–245° C. are obtained. Chromatography (silica gel, methylene chloride/methanol 3/1) of the neutralized mother liquor gives, in addition to 5-methylcytosine (14.95 g, melting point 264°–269° C.) a further 9.87 g (11.9% of theory) of the title compound; total yield: 36.3% of theory. 1H NMR (270 MHz, $d_6$-DMSO); δ[ppm]: 7.23 (s, 1H), 7.12 (s, broad, 1H), 6.70 (s, broad, 1H), 6.09 (m, 1H), 5.74 (m, 1H), 5.45 (m, 1H), 5.17 (s, 1H), 4.61 (m, 1H), 2.71 (m, 1H), 1.81 (s, 3H), 1.27 (m, 1H).

1.20.

Compound of the formula III in which A is thymin-1-yl, n is 1 and $R^4$ is hydrogen:

a) 0.4 g (1.54 mmol) of the compound of Example 1.18.1. is suspended in 15 ml of 2N sodium hydroxide solution and the suspension is stirred at room temperature for 12 hours. The resulting solution is neutralized with glacial acetic acid and concentrated to dryness and the residue is chromatographed over silica gel using methylene chloride/methanol 9/1. 316 mg (98.7% of theory) of 1-[(1RS,4SR)-4-hydroxy-cyclopent-2-en-1-yl]thymine of melting point 191°–192° C. are obtained.

b) 2.07 g (10 mmol) of the compound of Example 1.19. are suspended in 50 ml of water, 5.1 g (60 mmol) of sodium nitrite, 5 ml of glacial acetic acid and 10 ml of 1N aqueous hydrochloric acid are added and the mixture is stirred at room temperature for 10 hours. The reaction mixture is concentrated and the residue is boiled up several times with acetone. The acetone extracts are concentrated and the residue is chromatographed over silica gel using methylene chloride/methanol 9/1. 1.77 g (85.1% of theory) of 1-[(1RS, 4SR)-4-hydroxy-cyclopent-2-en-1-yl]thymine of melting point 191°–192° C. are obtained. 1H NMR (270 MHz, $d_6$-DMSO), δ[ppm]: 11.23 (s, 1H), 7.28 (s, 1H), 6.13 (m, 1H), 5.79 (m, 1H), 5.38 (m, 1H), 5.21 (d, 1H), 4.62 (m, 1H), 2.72 (m, 1H), 1.76 (s, 3H), 1.36 (m, 1H).

1.21.1. and 1.21.2.

Compounds of the formula III in which A is 3-[(1RS,4SR)-4-hydroxy-cyclopent-2-en-1-yl]thymin-1-yl, n is 1 and $R^4$ is hydrogen (1.21.1.) and in which A is thymin-3-yl, n is 1 and $R^4$ is hydrogen (1.21.2.):

80 ml of dry dimethylsulfoxide and 17.7 g (0.14 mol) of thymine are added to a solution of the palladium(0) catalyst (0.62 mol %) prepared in situ as described above in 70 ml of dry tetrahydrofuran; 11.5 g (0.14 mol) of epoxycyclopentene, dissolved in 50 ml of tetrahydrofuran, are then slowly added dropwise at 0° C. (4 hours). The reaction mixture is stirred at room temperature for 20 hours, poured into 300 ml of ethanol, stirred and filtered. The filtrate is concentrated and the residue is chromatographed over aluminum oxide using methylene chloride/methanol 19/1. This gives 15 g (36.9% of theory, based on the thymine employed) of 1,3-bis-[(1RS,4SR)-4-hydroxy-cyclopent-2-en-1-yl]thymine (diastereomer mixture) as an oil (compound 1.21.1.; 1H NMR (270 MHz, $d_6$-DMSO), δ[ppm]: 7.34 ("s", 1H), 6.15 (m, 1H), 5.83–5.75 (m, 3H), 5.67 (t, 1H), 5.41 (m, 1H), 5.22 (d, 1H), 4.76 (d, 1H), 4.62 (m, 2H), 2.76 (m, 1H), 2.50 (m, 1H), 1.93 (m, 1H), 1.80 (s, 3H), 1.38 (m, 1H)), and 0.9 g (3.1% of theory, based on the thymine employed) of 3-[(1RS,4SR)-4-hydroxy-cyclopent-2-en-1-yl]thymine of melting point 159°–160° C. (compound 1.21.2.). 1H NMR (270 MHz, $d_6$-DMSO), δ[ppm]: 10.85 (s, 1H), 7.29 (s, 1H), 5.78 (m, 2H), 5.62 (m, 1H), 4.77 (d, 1H), 4.58 (m, 1H), 2.50 (m, 1H), 1.89 (m, 1H), 1.76 (s, 3H).

1.22.

Compound of the formula III in which A is 3-benzyloxymethyl-thymin-1-yl, n is 1 and $R^4$ is hydrogen:

A solution of the palladium(0) catalyst described above is prepared (5 mol %) in 300 ml of dry tetrahydrofuran at 0° C. 24.6 g (0.1 mol) of 3-benzyloxymethylthymine (prepared by reaction of 1-acetylthymine with benzyl chloromethyl ether and triethylamine in dimethylformamide and subsequent aminolysis with aqueous methylamine, melting point 120° C.) are added to this solution. A solution of 12.3 g (0.15 mol) of epoxycyclopentene in 50 ml of tetrahydrofuran is then added dropwise (45 minutes). The resulting mixture is stirred at room temperature for 48 hours and concentrated and the residue is chromatographed over silica gel using ethyl acetate/cyclohexane 2/1. In addition to 16.2 g of 3-benzyloxymethylthymine, 2.59 g (23.1% of theory, based on the 3-benzyloxymethylthymine reacted) of 3-benzyloxymethyl-1-[(1RS,4SR)-4-hydroxy-cyclopent-2-en-1-yl] thymine of melting point 101°–104° C. are obtained. 1H NMR (270 MHz, $d_6$-DMSO), δ[ppm]: 7.31 (m, 6H), 6.15 (m, 1H), 5.79 (m, 1H), 5.43 (m, 1H), 5.36 (s, 2H), 5.23 (d, 1H), 4.64 (m, 1H), 4.60 (s, 2H), 2.75 (m, 1H), 1.80 (s, 3H), 1.37 (m, 1H).

1.23.

Compound of the formula III in which A is pyridin-2(1H)-on-1-yl, n is 1 and $R^4$ is hydrogen:

21 g (0.22 mol) of 2-pyridone are added at 0° C. to a solution of the palladium(0) catalyst prepared as above (2 mol % of palladium(II) acetate) in 200 ml of dry tetrahydrofuran, and 20.1 g (0.245 mol) of epoxycyclopentene, dissolved in 80 ml of tetrahydrofuran, are then added dropwise over a period of 2 hours, while stirring. The solution which forms is stirred at room temperature for 2 days and then concentrated, the residue is dissolved in methylene chloride, the solution is extracted by shaking with 1 A sodium carbonate solution and the organic phase is concentrated. The residue is chromatographed over silica gel using ethyl acetate/methanol 9/1. 7.2 g (18.49% of theory) of 1-[(1RS,4SR)-4-hydroxycyclopent-2-en-1-yl]pyridin-2(1H)-one are obtained as a viscous oil. 1H NMR (60 MHz, $d_6$-DMSO), δ[ppm]: 7.65–7.25 (m, 2H), 6.55–6.08 (m, 3H), 5.95–5.63 (m, 2H), 5.26 (d, 1H), 4.73 (m, 1H), 2.85 (m, 1H), 1.32 (m, 1H).

1.24.

Compound of the formula III in which A is pyridin-4(1H)-on-1-yl, n is 1 and $R^4$ is hydrogen:

If 4-hydroxypyridine is reacted as described in Example 1.23., 6.2 g (15.9% of theory) of 1-[(1RS,4SR)-4-hydroxy-cyclopent-2-en-1-yl]pyridin-4(1H)-one of melting point 188°–189° C. are obtained after chromatography (aluminum oxide, methylene chloride/methanol 9/1). 1H NMR (60 MHz, $d_6$-DMSO); δ[ppm]: 7.83–7.57 (m, 2H), 6.32–5.85 (m, 4H), 5.33 (d, 2H), 5.00 (m, 1H), 4.67 (m, 1H), 2.87 (m, 1H), 1.47 (m, 1H).

1.25.

Compound of the formula III in which A is 4,5-dichloropyridazin-3(2H)-on-2-yl, n is 1 and $R^4$ is hydrogen:

If 32.8 g (0.2 mol) of 4,5-dichloro-pyridazin-3(2H)-one are reacted by the above method, 19.5 g (39.47% of theory) of 4,5-dichloro-2-[(1RS,4SR)-4-hydroxy-cyclopent-2-en-1-yl]pyridazin-3(2H)-one of melting point 114°–115° C. are isolated. 1H NMR (270 MHz, $d_6$-DMSO); δ[ppm]: 8.22 (s, 1H), 6.0 (m, 1H), 5.78 (m, 1H), 5.57 (m, 1H), 5.06 (d, 1H), 4.69 (m, 1H), 2.78 (m, 1H), 1.62 (m, 1H).

1.26.

Compound of the formula III in which A is N-phthalimido, n is 1 and $R^4$ is hydrogen:

If 14.7 g (0.1 mol) of phthalimide are reacted in tetrahydrofuran (1 mol % of catalyst) by the above method, 10.9 g (47.6% of theory) of (1RS, 4SR)-4-hydroxy-1-phthalimido-cyclopent-2-ene of melting point 115°–116° C. are isolated. 1H NMR (60 MHz, $d_6$-DMSO); δ[ppm]: 7.88 (s, 4H), 5.93 (m, 2H), 5.25–4.40 (m, 4H), 2.58 (m, 1H), 2.0 (m, 1H).

1.27.

Compound of the formula III in which A is adenin-9-yl, n is 2 and $R^4$ is hydrogen:

The palladium(0) catalyst is prepared by bringing together 179.6 mg of palladium(II) acetate, 2 ml of triisopropyl phosphite and 1.06 ml of a 1.4 molar solution of butyllithium in n-hexane in 60 ml of dry tetrahydrofuran at 0° C. under argon. 60 ml of dry dimethylsulfoxide and 17.32 g (0.128 mol) of adenine are then added. After stirring for 15 minutes, 12.3 g (0.128 mol) of 3,4-epoxycyclohexene, dissolved in 40 ml of dry tetrahydrofuran, are added dropwise (3 hours). The suspension is stirred at room temperature for 24 hours, poured into 650 ml of ethanol and stirred and the precipitate (1 g of adenine) is filtered off with suction. The filtrate is concentrated and the residue is chromatographed over aluminum oxide using methylene chloride/methanol 15/1. 7.96 g (36.9% of theory) of 9-[(1RS,4SR)-4-hydroxycyclohex-2-en-1-yl]adenine of melting point 181° to 183° C. are obtained. 1H NMR (270 MHz, $d_6$-DMSO); δ[ppm]: 8.15 (s, 1H), 8.04 (s, 1H), 7.22 (s, 2H), 6.09 (m, 1H), 5.84 (m, 1H), 5.06 (m, 1H), 4.93 (d, 1H), 4.09 (m, 1H), 1.99 (m, 2H), 1.81 (m, 1H),, 1.56 (m, 1H).

1.28.1.

Compound of the formula IV in which A is cytosin-1-yl and $R^4$ is hydrogen:

27.75 g (0.25 mol) of cytosine are reacted with 2 mol % of the palladium(0) catalyst produced in situ and 0.275 mol of 3,4-epoxycyclohexene in a mixture of in each case 120 ml of dry tetrahydrofuran and dimethylsulfoxide as described in the preceding example. The crude product is filtered off with suction and washed with tetrahydrofuran and ethanol, and gives, after crystallization from ethanol, 29 g (56% of theory) of 1-[(1RS,4SR)-2-hydroxycyclohex-5-en-1-yl]cytosine of melting point 264° C. (decomposition). 1H NMR (270 MHz, $d_6$-DMSO); δ[ppm]: 7.27 (d, 1H), 6.94 (d, 2H), 5.96 (m, 1H), 5.63 (d, 1H), 5.35 (m, 1H), 5.14 (m, 1H), 4.89 (d, 1H), 3.93 (s, broad, 1H), 2.21 (m, 1H), 1.94 (m, 1H), 1.74 (m, 2H).

1.28.2.

Compound of the formula III in which A is cytosin-1-yl, n is 2 and $R^4$ is hydrogen:

4.3 g (6.6% of theory) of 1-[(1RS,4SR)-4-hydroxy-cyclohex-2-en-1-yl]cytosine of melting point 224°–226° C. are isolated from the mother liquors obtained during working up of compound 1.28.1. by chromatography over silica gel using methylene chloride/methanol 3/1. 1H NMR (270 MHz, $d_6$-DMSO); δ[ppm]: 7.44 (d, 1H), 7.00 (s, 2H), 6.04 (m, 1H), 5.70 (d, 1H), 5.55 (m, 1H), 4.97 (m, 1H), 4.86 (d, 1H), 4.00 (m, 1H), 1.70 (m, 3H), 1.50 (m, 1H).

1.29.1.

Compound of the formula IV in which A is uracil-1-yl and $R^4$ is hydrogen:

4.14 g (0.02 mol) of the compound of Example 1.28.1. are dissolved with 8.28 g (0.12 mol) of sodium nitrite in 130 ml of water, 13 ml of glacial acetic acid and 20 ml of 1N aqueous hydrochloric acid, and the solution is stirred at room temperature for 2 days. The reaction solution is concentrated and the residue is stirred with a little ice-cold water, filtered off with suction and washed with a little cold water. 3.6 g (86.5% of theory) of 1-[(1RS,2SR)-2-hydroxy-cyclohex-5-en-1-yl]uracil of melting point 203° C. are obtained. 1H NMR (270 MHz, $d_6$-DMSO); δ[ppm]: 11.18 (s, 1H), 7.27 (d, 1H), 6.04 (m, 1H), 5.50 (m, 1H), 5.39 (m, 1H), 5.07 (d, 1H), 5.03 (m, 1H), 3.96 (m, 1H), 2.21 (m, 1H), 1.95 (m, 1H), 1.76 (m, 2H).

1.29.2.

Compound of the formula III in which A is uracil-1-yl, n is 2 and $R^4$ is hydrogen:

1.55 g (7.5 mmol) of the compound of Example 1.28.2. are dissolved with 3.1 g (45 mmol) of sodium nitrite in 50 ml of water with 5 ml of glacial acetic acid and 7.5 ml of 1N aqueous hydrochloric acid, and the solution is stirred at room temperature for 48 hours. The resulting solution is concentrated and the residue is chromatographed over silica gel using methylene chloride/methanol 5/1. 1.35 g (86.5% of theory) of 1-[(1RS,4SR)-4-hydroxycyclohex-2-en-1-yl]uracil of melting point 161°–162° C. are obtained. 1H NMR (60 MHz, $d_6$-DMSO); δ[ppm]: 11.33 (s, 1H), 7.53 (d, 1H), 6.13 (m, 1H), 5.8–5.5 (m, 2H), 4.92 (m, 2H), 4.03 (m, 1H), 1.75 (m, 4H).

1.30.1.

Compound of the formula IV in which A is N-phthalimido and $R^4$ is hydrogen:

If 19.11 g (0.13 mol) of phthalimide are reacted with 0.6 mol % of the palladium(0) catalyst prepared in situ as described above and one equivalent of 3,4-epoxycyclohexene in tetrahydrofuran first at 0° C. and then for 4 hours at the reflux temperature, 1.45 g (4.6% of theory) of [(1RS, 2SR)-2-hydroxy-1-phthalimido-cyclohex-5-ene of melting point 112° to 114° C. are obtained after purification by chromatography over silica gel using ethyl acetate/cyclohexane 3/2. 1H NMR (270 MHz, $d_6$-DMSO); δ[ppm]: 7.83 (m, 4H), 5.90 (m, 1H), 5.63 (m, 1H), 4.84 (d, 1H), 4.75 (m, 1H), 3.90 (m, 1H), 2.27 (m, 1H), 2.1–1.65 (m, 3H).

1.30.2.

Compound of the formula III in which A is N-phthalimido, n is 2 and $R^4$ is hydrogen:

Continued purification of the reaction batch 1.30.1. by chromatography gives 9.62 g (33% of theory) of (1RS, 4SR)-4-hydroxy-1-phthalimido-cyclohex-2-ene of melting point 126°–129° C. 1H NMR (270 MHz, $d_6$-DMSO); δ[ppm]: 7.85 (m, 4H), 5.83 (m, 1H), 5.72 (m, 1H), 4.76 (d, 1H), 4.60 (m, 1H), 4.04 (m, 1H), 2.24 (m, 1H), 1.90–1.55 (m, 3H).

1.31.

Compound of the formula III in which A is guanin-9-yl, n is 2 and $R^4$ is hydrogen:

7.56 g (50 mmol) of guanine are reacted with 2 mol % of the palladium(0) catalyst prepared in situ as above and one equivalent of 3,4-epoxycyclohexene in tetrahydrofuran first at 0° C. and then for 8 hours under reflux temperature, and the mixture is then poured into methanol. The reaction mixture is concentrated and the residue is taken up in 2-propanol and filtered off with suction. The residue is recrystallized first from ethanol with active charcoal and then from water. 3.1 g (25.1% of theory) of 9-[(1RS,4SR)-4-hydroxy-cyclohex-2-en-1-yl]guanine of melting point >300° C. are obtained. 1H NMR (270 MHz, $d_6$-DMSO); δ[ppm]: 10.57 (s, 1H), 7.60 (s, 1H), 6.46 (s, 2H), 6.05 (m, 1H), 5.77 (m, 1H), 4.91 (d, 1H), 4.79 (m, 1H), 4.06 (m, 1H), 1.95–1.75 (m, 3H), 1.53 (m, 1H).

1.32.

1-[(4RS)-4-Hydroxy-cyclohex-2-en-1-yl]thymine:

6.3 g (50 mmol) of thymine are treated with 2 mol % of the palladium(0) catalyst prepared in situ as described above and with one equivalent of 3,4-epoxycyclohexene in tetrahydrofuran first at 0° C. and then for 4 hours at the reflux temperature. Methanol is added to the reaction mixture, the suspension is filtered, the filtrate is concentrated and the residue is chromatographed over silica gel using methylene chloride/methanol 20/1. 1.8 g (16.2% of theory) of 1-[(4RS)-4-hydroxy-cyclohex-1-en-1-yl]thymine of melting point 223° C. are obtained. 1H NMR (270 MHz, $d_6$-DMSO); δ[ppm]: 11.23 (s, 1H), 7.69 (s, 1H), 4.59 (m, 1H), 2.84 (t, 1H), 2.42–1.81 (m, 6H), 1.79 (s, 3H), 1.61 (m, 1H).

Acyl Derivatives

The acyl derivatives are prepared by reaction of the corresponding acid anhydride (for example acetic anhydride) with the particular alcohol under catalysis with N,N-dimethylaminopyridine in a solvent, such as, for example, methylene chloride, or by reaction with an acid anhydride in pyridine.

2.1.1.

Compound of the formula V in which A is $N^6$-acetyl-adenin-9-yl, n is 1 and $R^5$ is acetyl:
Colorless crystals, melting point: 153°–154° C.

2.1.2.

Compound of the formula V in which A is $N^6$-diacetyl-adenin-9-yl, n is 1 and $R^5$ is acetyl:
Oil, 1H NMR (270 MHz, $d_6$-DMSO); δ[ppm]: 8.98 (s, 1H), 8.57 (s, 1H), 6.38 (m, 1H), 6.31 (m, 1H), 5.75 (m, 1H), 5.67 (m, 1H), 3.10 (m, 1H), 2.25 (s, 6H), 2.07 (m, 1H), 2.03 (s, 3H).

2.1.3.

Compound of the formula V in which A is adenin-9-yl, n is 1 and $R^5$ is acetyl:
Colorless powder, melting point: 130°–133° C.

2.1.4.

Compound of the formula V in which A is $N^6$-acetyl-adenin-9-yl, n is 1 and $R^5$ is hydrogen:
Colorless crystals, melting point: 134°–136° C., 1H NMR (60 MHz, $d_6$-DMSO); δ[ppm]: 10.6 (s, 1H), 8.67 (s, 1H), 8.40 (s, 1H), 6.13 (m, 2H), 5.57 (m, 1H), 5.35 (d, 1H), 4.73 (m, 1H), 2.95 (m, 1H), 2.27 (s, 3H), 1.73 (m, 1H).

2.2.

Compound of the formula V in which A is hypoxanthin-9-yl, n is 1 and $R^5$ is acetyl:
Colorless crystals, melting point: 215°–218° C.

2.3.

Compound of the formula V in which A is 6-chloropurin-9-yl, n is 1 and $R^5$ is acetyl:
Colorless crystals, melting point: 114°–115° C.

2.4.1.

Compound of the formula V in which A is 2-acetamido-6-chloro-purin-9-yl, n is 1 and $R^5$ is acetyl:
Colorless crystals, melting point: 180°–181° C.

2.4.2.

Compound of the formula V in which A is 2-acetamido-6-chloro-purin-9-yl, n is 1 and $R^5$ is hydrogen:
Pale yellow crystals, melting point: 191°–193° C., 1H NMR (270 MHz, $d_6$-DMSO); δ[ppm]: 10.83 (s, 1H), 8.43 (s, 1H), 6.21 (m, 1H), 6.03 (m, 1H), 5.20 (d, 1H), 4.75 (m, 1H), 2.93 (m, 1H), 2.21 (s, 3H), 1.82 (m, 1H).

2.4.3.

Compound of the formula V in which A is 2-amino-6-chloropurin-9-yl, n is 1 and $R^5$ is acetyl:
Light yellow crystals, melting point: 183°–185° C., 1H NMR (60 MHz, $d_6$-DMSO); δ[ppm]: 8.0 (s, 1H), 6.95 (s, 2H), 6.33 (m, 2H), 5.80–5.32 (m, 2H), 3.28–2.73 (m, 1H), 2.07 (s, 1H), 1.93 (m, 1H).

2.5.

Compound of the formula V in which A is 2-acetamido-6-ethoxy-purin-9-yl, n is 1 and $R^5$ is hydrogen:
Pale yellow crystals, melting point: 126°–128° C., 1H NMR (270 MHz, $d_6$-DMSO); δ[ppm]: 10.32 (s, 1H), 8.13 (s, 1H), 6.19 (m, 1H), 6.0 (m, 1H), 5.42 (m, 1H), 5.21 (d, 1H), 4.73 (m, 1H), 4.57 (q, 2H), 2.90 (m, 1H), 2.23 (s, 3H), 1.77 (m, 1H), 1.40 (t, 3H).

2.6.1.

Compound of the formula V in which A is $N^2$-acetyl-guanin-9-yl, n is 1 and $R^6$ is acetyl:
Colorless crystals, melting point: 247° C.

2.6.2.

Compound of the formula V in which A is guanin-9-yl, n is 1 and $R^5$ is acetyl:
Colorless crystals, melting point: 243° C., 1H NMR (270 MHz, $d_6$-DMSO); δ[ppm]: 10.58 (s, 1H), 7.51 (s, 1H), 6.45 (s, 2H), 6.23 (m, 2H), 5.62 (m, 1H), 5.30 (m, 1H), 2.97 (m, 1H), 2.02 (s, 3H), 1.80 (m, 1H).

2.7.

Compound of the formula V in which A is 5-benzyloxymethyl-1H-imidazo[4,5-d]pyridazin-4(5H)-on-1-yl, n is 1 and $R^5$ is acetyl:
Pale red crystals, melting point: 105° C.

2.8.1.

Compound of the formula V in which A is $N^4$-acetyl-cytosin-1-yl, n is 1 and $R^5$ is acetyl:
Colorless crystals, melting point: 196° C.

2.8.2.

Compound of the formula V in which A is cytosin-1-yl, n is 1 and $R^4$ is acetyl:
Pale yellow crystals, melting point: 48°–52° C. (decomposition), 1H NMR (270 MHz, $d_6$-DMSO); δ[ppm]: 7.41 (d, 1H), 7.02 (s, 2H), 6.09 (m, 1H), 5.75 (m, 1H), 5.72 (d, 1H), 5.45 (m, 1H), 4.63 (m, 1H), 2.72 (m, 1H), 1.91 (s, 3H), 1.27 (m, 1H).

2.9.1.

Compound of the formula V in which A is uracil-1-yl, n is 1 and $R^5$ is acetyl:
Colorless crystals: melting point: 131°–136° C.

2.9.2.

Compound of the formula V in which A is 3-(4-acetoxycyclo-pent-2-en-1-yl)uracil-1-yl, n is 1 and $R^5$ is acetyl:
Colorless powder, melting point: 148° C.

2.10.

Compound of the formula V in which A is thymin-1-yl, n is 1 and $R^5$ is acetyl:
Colorless crystals, melting point: 149°–150° C.; 1H NMR (270 MHz, $d_6$-DMSO), δ[ppm]: 11.27 (s, 1H), 7.12 (s, 1H), 6.20 (m, 1H), 6.08 (m, 1H), 5.54 (m, 1H), 5.45 (m, 1H), 2.84 (m, 1H), 2.03 (s, 3H), 1.78 (s, 3H), 1.57 (m, 1H).

2.11.

Compound of the formula V in which A is 3-(4-acetoxycyclo-pent-2-en-1-yl)thymin-1-yl, n is 1 and $R^5$ is acetyl:
Oil, 1H NMR (270 MHz, $d_6$-DMSO), δ[ppm]: 7.15 (s, 1H), 6.21 (m, 1H), 6.09 (m, 1H), 6.04 (m, 1H), 5.8–5.67 (m, 2H), 5.61–5.42 (m, 3H), 2.88 (m, 1H), 2.64 (m, 1H), 2.11 (m, 1H), 2.03 (s, 6H), 1.81 (s, 3H), 1.6 (m, 1H).

2.12.

Compound of the formula V in which A is 4,5-dichloropyridazin-3(2H)-on-2-yl, n is 1 and $R^5$ is acetyl:
Colorless crystals, melting point: 108° C.

2.13.

Compound of the formula V in which A is pyridin-4(1H)-on-1-yl, n is 1 and $R^5$ is acetyl:
Colorless crystals, melting point 109°–110° C.

2.14.

Compound of the formula V in which A is pyridin-2(1H)-on-1-yl, n is 1 and $R^4$ is acetyl:
Colorless oil; 1H NMR (60 MHz, $d_6$-DMSO), δ[ppm]: 7.37 (m, 2H), 6.60–6.08 (m, 4H), 5.95–5.53 (m, 2H), 2.92 (m, 1H), 2.03 (s, 3H), 1.47 (m, 1H).

2.15.

Compound of the formula V in which A is N-phthalimido, n is 1 and $R^5$ is acetyl:
Colorless crystals, melting point: 85°–86° C.

2.16.

Compound of the formula V in which A is guanin-9-yl, n is 2 and $R^5$ is acetyl:
Colorless crystals, melting point: >290° C., 1H NMR (270 MHz, $d_6$-DMSO), δ[ppm]: 10.81 (s, 1H), 7.81 (s, 1H), 6.18–6.03 (m, 4H), 5.23 (m, 2H), 2.16–1.83 (m, 7H), 1.74–1.60 (m, 1H).

2.17.

Compound of the formula VI in which A is $N^4$-acetyl-cytosin-1-yl, n is 2 and $R^5$ is acetyl:
Colorless crystals, melting points 211° C.

2.18.

Compound of the formula V in which A is N-phthalimido, n is 2 and $R^5$ is acetyl:
Colorless crystals, melting point: 153°–155° C.

Triol Derivatives

To prepare the compounds of the formulae VIIa or Ia and VIIIa or IIa, 50 mmol of the unsaturated compounds of the formulae V or III or VI or IV are dissolved or suspended with 100–150 mmol of N-methyl-morpholine N-oxide hydrate in a mixture of 200 ml of water and 100 ml of tetrahydrofuran (it being possible to add acetone if required in order to achieve a homogeneous solution), 0.5–2.0 mol % of a 1% strength solution of osmium tetroxide in water is added and the mixture is stirred at room temperature for 5 hours to 6 days. 100–200 mmol of sodium bisulfite are then added to the reaction mixture, the mixture is concentrated and the residue is purified by chromatography over silica gel.

3.1.1.

Compound of the formula Ia in which A is adenin-9-yl, n is 1 and $R^1$, $R^2$ and $R^3$ are hydrogen:
cis-Hydroxylation of the compound of Example 2.1.1. carried out by the method described above gives a 52.7% yield of $N^6$-acetyl-9-[(1RS,2SR,3SR,4SR)-4-acetoxy-2,3-dihydroxy-cyclo-pent-1-yl]adenine (compound of the formula VIIa in which A is $N^6$-acetyl-adenin-9-yl, n is 1 and $R^5$ is acetyl) of melting point 193°–195° C. This compound is suspended in pyridine, concentrated aqueous ammonia is added and the mixture is stirred at 60° C. for 6 hours. After crystallization from ethanol/water 9/1, an 86% yield of 9-[(1RS,2SR,3RS,4SR)-2,3,4-trihydroxycyclo-pent-1-yl] adenine of melting point 282° C. (hemihydrate), is obtained. 1H NMR (270 MHz, $d_6$-DMSO), δ[ppm]: 8.17 (s, 1H), 8.13 (s, 1H), 7.23 (s, 2H), 5.36 (d, 1H), 5.01 (d, 1H), 4.87 (d, 1H), 4.7 (m, 1H), 4.53 (m, 1H), 3.92 (m, 1H), 3.78 (m, 1H), 2.62 (m, 1H), 1.83 (m, 1H).

3.1.2.

Compound of the formula Ia in which A is $N^6$-acetyl-adenin-9-yl, n is 1, $R^1$-$R^2$ is dimethylmethylene and $R^3$ is acetyl:
Reaction of the compound of the formula VIIa of Example 3.1.1. with 2,2-dimethoxypropane in acetone with p-toluenesulfonic acid as the catalyst gives $N^6$-acetyl-9-[(1RS,2SR,3SR,4SR)-4-acetoxy-2,3-dihydroxy-2,3-O-isopropylidene-cyclopent-1-yl]adenine of melting point 82°–83° C. (hemihydrate, 54.4% of theory). 1H NMR (270 MHz, $d_6$-DMSO), δ[ppm]: 10.71 (s, 1H), 8.68 (s, 1H), 8.59 (s, 1H), 5.22 (m, 1H), 5.1–5.0 (m, 2H), 4.82 (d, 1H), 2.72 (m, 1H), 2.44 (m, 1H), 2.28 (s, 3H), 1.93 (s, 3H), 1.50 (s, 3H), 1.29 (s, 3H).

3.1.3.

Compound of the formula Ia in which A is adenin-9-yl, n is 1, $R^1$-$R^2$ is dimethylmethylene and $R^3$ is acetyl:
In addition to the compound of Example 3.1.2., 9-[(1RS,2SR,3SR,4SR)-4-acetoxy-2,3-dihydroxy-2,3-O-isopropylidene-cyclopent-1-yl]adenine of melting point 229°–230° C. is obtained from the above reaction in a yield of 23.3%. 1H NMR (270 MHz, $d_6$-DMSO), δ[ppm]: 8.25 (s, 1H), 8.19 (s, 1H), 7.4 (s, 2H), 5.18 (m, 1H), 5.04 (m, 1H), 4.89 (m, 1H), 4.80 (d, 1H), 2.68 (m, 1H), 2.40 (m, 1H), 1.96 (s, 3H), 1.49 (s, 3H), 1.28 (s, 3H).

3.1.4.

Compound of the formula Ia in which A is adenin-9-yl, n is 1, $R^1$-$R^2$ is dimethylmethylene and $R^3$ is hydrogen:
Ammonolysis of the compound of Example 3.1.3. gives 9-[(1RS,2SR,3RS,4SR)-2,3,4-trihydroxy-2,3-O-isopropylidene-cyclopent-1-yl]adenine (68.1% of theory, melting point: 124° C. (decomposition)). 1H NMR (400 MHz, $d_6$-DMSO), δ[ppm]: 8.25 (s, 1H), 8.14 (s, 1H), 7.18 (s, 2H), 5.51 (d, 1H), 4.94 (m, 1H), 4.82 (m, 1H), 4.55 (d, 1H), 4.17 (m, 1H), 2.52 (m, 1H), 2.19 (m, 1H), 1.43 (s, 3H), 1.23 (s, 3H).

3.2.

Compound of the formula Ia in which A is hypoxanthin-9-yl, n is 1 and $R^1$, $R^2$ and $R^3$ are hydrogen:
cis-Hydroxylation of the compound of Example 2.2. carried out by the method described above gives a 98.6% yield of 9-[(1RS,2SR,3SR,4SR)-4-acetoxy-2,3-dihydroxy-cyclopent-1-yl]hypoxanthine (compound of the formula VIIa in which N is hypoxanthin-9-yl, n is 1 and $R^4$ is acetyl) of melting point 240°–242° C. as the hemihydrate. This compound is suspended in pyridine, concentrated aqueous ammonia is added and the mixture is stirred at 60° C. for 6 hours. A 97.6% yield of 9-[(1RS,2SR,3RS,4SR)-2,3,4-trihydroxy-cyclopent-1-yl]hypoxanthine (hydrate) of melting point 198° to 201° C. is obtained.

3.3.

Compound of the formula Ia in which A is $N^6$-methyl-adenin-9-yl, n is 1 and $R^1$, $R^2$ and $R^3$ are hydrogen:

cis-Hydroxylation of the compound of Example 2.3.—carried out as described above—gives a 61.4% yield of 6-chloro-9-[(1RS,2SR,3SR,4SR)-4-acetoxy-2,3-dihydroxy-cyclopent-1-yl]purine (compound of the formula VIIa in which A is 6-chloropurin-9-yl, n is 1 and $R^5$ is acetyl) of melting point 103°–104° C. This compound is dissolved in methanol, 40% strength aqueous methylamine is added and the mixture is stirred at the reflux temperature for one hour. Chromatography (silica gel, methylene chloride/methanol 2/1) gives a 78% yield of $N^6$-methyl-9-[(1RS,2SR,3RS,4SR)-trihydroxy-cyclopent-1-yl]adenine of melting point 180° C. (decomposition). 1H NMR (270 MHz, $d_6$-DMSO), δ[ppm]: 8.2 (s, 1H), 8.14 (s, 1H), 7.67 (s, 1H), 5.35 (d, 1H), 4.98 (d, 1H), 4.84 (d, 1H), 4.68 (m, 1H), 4.51 (m, 1H), 3.90 (m, 1H), 3.74 (m, 1H), 2.98 (s, 3H), 2.61 (m, 1H), 1.83 (m, 1H).

3.4.

Compound of the formula Ia in which A is 2-aminopurin-9-yl, n is 1 and $R^1$, $R^2$ and $R^3$ are hydrogen:

cis-Hydroxylation of the compound of Example 2.4.1.—carried out as described above—gives a 41% yield of 2-acetamido-6-chloro-9-[(1RS,2SR,3SR,4SR)-4-acetoxy-2,3-dihydroxy-cyclopent-1-yl]purine (compound of the formula VIIa in which A is 2-acetamido-6-chloro-purin-9-yl, n is 1 and $R^5$ is acetyl) of melting point 198° C. This compound is suspended in methanol with the addition of triethylamine and palladium-on-charcoal and is hydrogenated under normal pressure. Hydrogenolysis gives an 85% yield of 2-acetamido-9-[(1RS,2SR,3SR,4SR)-4-acetoxy-2,3-dihydroxy-cyclopent-1-yl]purine (compound of the formula VIIa in which A is 2-acetamidopurin-9-yl, n is 1 and $R^5$ is acetyl) of melting point 222°–223° C. This diacetyl compound is dissolved in methanol with the addition of aqueous methylamine and is boiled under reflux for one hour. A 71% yield of 2-amino-9-[(1RS,2SR,3RS,4SR)-2,3,4-trihydroxy-cyclopent-1-yl]purine of melting point 153°–155° C. is obtained. 1H NMR (270MHz, $d_6$-DMSO), δ[ppm]: 8.57 (s, 1H), 8.12 (s, 1H), 6.47 (s, 1H), 5.15 (d, 1H), 4.99 (d, 1H), 4.81 (d, 1H), 4.66 (m, 1H), 4.45 (m, 1H), 3.93 (m, 1H), 3.76 (m, 1H), 2.57 (m, 1H), 1.72 (m, 1H).

3.5.

Compound of the formula Ia in which A is guanin-9-yl, n is 1 and $R^1$, $R^2$ and $R^3$ are hydrogen:

cis-Hydroxylation of the compound of Example 2.6.1.—carried out as described above—gives an 88% yield of $N^2$-acetyl-9-[(1RS,2SR,3SR,4SR)-4-acetoxy-2,3-dihydroxy-cyclopent-1-yl]guanine (compound of the formula VIIa in which N is $N^2$-acetyl-guanin-9-yl, n is 1 and $R^5$ is acetyl) of melting point 234° C. This compound is treated with methanol and aqueous methylamine solution as described above and, after crystallization from ethanol/water, gives a 69% yield of 9-[(1RS,2SR,3RS,4SR)-2,3,4-trihydroxy-cyclopent-1-yl]guanine (hemihydrate) of melting point 295° C. 1H NMR (270 MHz, $d_6$-DMSO), δ[ppm]: 10.50 (s, 1H), 7.74 (s, 1H), 6.36 (s, 2H), 5.14 (d, 1H), 4.95 (d, 1H), 4.77 (d, 1H), 4.51 (m, 1H), 4.37 (m, 1H), 3.86 (m, 1H), 3.72 (m, 1H), 2.53 (m, 1H), 1.61 (m, 1H).

3.6.

Compound of the formula Ia in which A is 1H-imidazo-[4,5-d]pyridazin-4(5H)-on-1-yl, n is 1 and $R^1$, $R^2$ and $R^3$ are hydrogen:

cis-Hydroxylation of the compound of Example 1.15.—carried out as described above—gives an 87% yield of 5-benzyloxymethyl-1-[(1RS,2SR,3RS,4SR)-2,3,4-trihydroxy-cyclopent-1-yl]imidazo[4,5-d]pyridazin-4(5H)-one (compound of the formula VIIa in which A is 5-benzyloxymethyl-1H-imidazo[4,5-d]pyridazin-4(5H)-on-1-yl, n is 1 and $R^5$ is hydrogen) as a vitreous foam. This compound is hydrogenated in methanol using palladium-on-charcoal as the catalyst to give a 79% yield of 1-[(1RS,2SR,3RS,4SR)-2,3,4-trihydroxy-cyclo-pent-1-yl]imidazo[4,5-d]-pyridazin-4(5H)-one as a foam. The title compound can also be obtained if the compound of Example 2.7. is subjected to cis-hydroxylation by the method described above and, thereafter the benzyloxymethyl protective group is split off hydrogenolytically and the acetyl protective group is split off hydrolytically.

3.7.

Compound of the formula Ia in which A is cytosin-1-yl, n is 1 and $R^1$, $R^2$ and $R^3$ are hydrogen:

cis-Hydroxylation of the compound of Example 2.8.1.—carried out as described above—gives a 49% yield of $N^4$-acetyl-1-[(1RS,2SR,3SR,4SR)-4-acetoxy-2,3-dihydroxy-cyclopent-1-yl]cytosine (compound of the formula VIIa in which N is $N^4$-acetyl-cytosin-1-yl, n is 1 and $R^5$ is acetyl) of melting point 98° to 100° C. This compound is treated with concentrated aqueous ammonia in pyridine at 60° C. to give an 84% yield of 1-[(1RS,2SR,3SR,4SR)-4-acetoxy-2,3-dihydroxy-cyclopent-1-yl]cytosine (compound of the formula VIIa in which N is cytosin-1-yl, n is 1 and $R^5$ is acetyl) of melting point 121°–124° C. Reaction of this compound with aqueous methylamine in methanol at the reflux temperature gives a 78% yield of 1-[(1RS,2SR,3RS,4SR)-2,3,4-trihydroxy-cyclopent-1-yl]-cytosine of melting point 155° C. (decomposition). 1H NMR (270 MHz, $d_6$-DMSO), δ[ppm]: 7.64 (d, 1H), 7.19 (s, broad, 2H), 5.76 (d, 1H), 5.20 (s, broad, 1H), 4.76 (s, broad, 2H), 4.59 (m, 1H), 4.19 (m, 1H), 3.78 (m, 1H), 3.63 (m, 1H), 2.40 (m, 1H), 1.38 (m, 1H). The title compound can also be obtained by cis-hydroxylation of the compound of Example 1.16.

3.8.

Compound of the formula Ia in which A is uracil-1-yl, n is 1 and $R^1$, $R^2$ and $R^3$ are hydrogen:

cis-Hydroxylation of the compound of Example 1.17.—carried out as described above—gives a 79% yield of 1-[(1RS,2SR,3RS,4SR)-2,3,4-trihydroxy-cyclopent-1-yl] uracil of melting point 229°–230° C. 1H NMR (270 MHz, $d_6$-DMSO), δ[ppm]: 11.18 (s, 1H), 7.66 (d, 1H), 5.65 (d, 1H), 5.11 (d, 1H), 4.92 (d, 1H), 4.78 (d, 1H), 4.73 (m, 1H), 4.11 (m, 1H), 3.82 (m, 1H), 3.65 (m, 1H), 2.42 (m, 1H), 1.34 (m, 1H).

3.9.

Compound of the formula Ia in which A is thymin-1-yl, n is 1 and $R^1$, $R^2$ and $R^3$ are hydrogen:

cis-Hydroxylation of the compound of Example 2.10.—carried out as described above—gives a 78% yield of 1-[(1RS,2SR,3SR,4SR)-4-acetoxy-2,3-dihydroxy-cyclo-pent-1-yl]thymine (compound of the formula VIIa in which N is thymin-1-yl, n is 1 and $R^4$ is acetoxy) of melting point 58°–61° C. 1H NMR (270 MHz, $d_6$-DMSO), δ[ppm]: 11.30 (s, 1H), 7.49 (d, 1H), 5.15 (d, 1H), 5.08 (d, 1H), 4.74 (m, 1H), 4.63 (m, 1H), 4.16 (m, 1H), 3.85 (m, 1H), 2.43 (m, 1H), 2.05 (s, 3H), 1.80 (s, 3H), 1.58 (m, 1H). This compound is treated with aqueous methylamine solution in pyridine to give an 84% yield of 1-[(1RS,2SR,3RS,4SR)-2,3,4-trihydroxy-cyclopent-1-yl]thymine of melting point 201°–202° C. 1H NMR (270 MHz, $d_6$-DMSO), δ[ppm]: 11.18 (s, 1H), 7.54 (s, 1H), 5.10 (d, 1H), 4.87 (d, 1H), 4.77 (d, 1H), 4.70 (m, 1H), 4.14 (m, 1H), 3.81 (m, 1H), 3.66 (m, 1H), 2.40 (m, 1H), 1.79 (s, 3H), 1.34 (m, 1H).

3.10.1.

Compound of the formula Ia in which A is 4,5-dichloro-pyridazin-3(2H)-on-2-yl, n is 1 and $R^1$, $R^2$ and $R^3$ are hydrogen:

cis-Hydroxylation of the compound of Example 1.25.— carried out as described above—gives a 59% yield of 4,5-dichloro-2-[(1RS,2SR,3RS,4SR)-2,3,4-trihydroxy-cyclopent-1-yl]pyridazin-3(2H)-one of melting point 163° C. 1H NMR (270 MHz, $d_6$-DMSO), δ[ppm]: 8.26 (s, 1H), 5.17 (m, 1H), 4.95 (d, 1H), 4.82 (d, 1H), 4.77 (d, 1H), 4.29 (m, 1H), 3.84 (m, 1H), 3.67 (m, 1H), 2.41 (m, 1H), 1.49 (m, 1H).

3.10.2.

Compound of the formula Ia in which A is 4-chloro-5-methoxy-pyridazin-3(2H)-on-2-yl, n is I and $R^1$, $R^2$ and $R^3$ are hydrogen:

cis-Hydroxylation of the compound of Example 2.12.— carried out as described above—gives a 49% yield of 4,5-dichloro-2-[(1RS,2SR,3SR,4SR)-4-acetoxy-2,3-dihydroxy-cyclopent-1-yl]pyridazin-3(2H)-one (compound of the formula VIIa in which A is 4,5-dichloro-pyridazin-3(2H)-on-2-yl, n is 1 and $R^5$ is acetyl) of melting point 119°–122° C. This compound is dissolved in methanol with 0.1 equivalent of KCN and the solution is stirred at room temperature for 12 hours. The mixture is then rendered alkaline by addition of an anion exchanger (OH⁻ form), and after 5 minutes is neutralized by addition of a cation exchanger (H⁺ form). The ion exchanger is filtered off, the filtrate is concentrated and the residue is chromatographed over silica gel (ethyl acetate/methanol 20/1). In addition to 38% of the compound of Example 3.10.1., 27% of 4-chloro-5-methoxy-2-[(1RS,2SR,3RS,4SR)-2,3,4-trihydroxy-cyclopent-1-yl]pyridazin-3(2H)-one of melting point 166°–168° C. are isolated. 1H NMR (270 MHz, $d_6$-DMSO), δ[ppm]: 8.32 (s, 1H), 5.19 (m, 1H), 4.94 (d, 1H), 4.75 (d, 1H), 4.73 (d, 1H), 4.30 (m, 1H), 4.07 (s, 3H), 3.84 (m, 1H), 3.68 (m, 1H), 2.87 (m, 1H), 1.44 (m, 1H).

3.11.

Compound of the formula Ia in which A is pyridin-4(1H)-on-1-yl, n is 1 and $R^1$, $R^2$ and $R^3$ are hydrogen:

cis-Hydroxylation of the compound of Example 2.13.— carried out as described above—gives an 81% yield of 1-[(1RS,2SR,3SR,4SR)-4-acetoxy-2,3-dihydroxy-cyclopent-1-yl]pyridin-4(1H)-one (compound of the formula VIIa in which N is pyridin-4(1H)-on-1-yl, n is 1 and $R^5$ is acetyl) of melting point 191° to 196° C. This compound is dissolved in methanol with the addition of aqueous methylamine solution and the solution is heated under reflux for 90 minutes. Working up gives a 79% yield of 1-[(1RS,2SR,3RS,4SR)-2,3,4-trihydroxy-cyclopent-1-yl]-pyridin-4(1H)-one of melting point 186°–188° C. 1H NMR (270 MHz, $d_6$-DMSO), δ[ppm]: 7.70 (d, 2H), 6.01 (d, 2H), 5.24 (d, 1H), 5.06 (d, 1H), 4.95 (d, 1H), 4.14 (m, 2H), 3.86 (m, 1H), 3.68 (m, 1H), 2.60 (m, 1H), 1.53 (m, 1H).

3.12.

Compound of the formula Ia in which A is pyridin-2(1H)-on-1-yl, n is 1 and $R^1$, $R^2$ and $R^3$ are hydrogen:

cis-Hydroxylation of the compound of Example 2.14.— carried out as described above—gives an 81% yield of 1-[(1RS, 2SR, 3SR, 4SR) -4-acetoxy-2,3-dihydroxy-cyclopent-1-yl]pyridin-2(1H)-one (compound of the formula VIIa in which N is pyridin-2(1H)-on-1-yl, n is 1 and $R^5$ is acetyl) of melting point 133° to 135° C. This compound is dissolved in methanol with the addition of aqueous methylamine and the solution is kept at the reflux temperature for 90 minutes. 1-[(1RS,2SR,3RS,4SR)-2,3,4-trihydroxy-cyclopent-1-yl]-pyridin-2(1H)-one of melting point 138°–140° C. is obtained in an 80% yield. 1H NMR (270 MHz, $d_6$-DMSO), δ[ppm]: 7.72 (m, 1H), 7.37 (m, 1H), 6.31 (m, 2H), 5.19 (d, 1H), 5.03 (m, 1H), 4.77 (m, 2H), 4.28 (m, 1H), 3.85 (m, 1H), 3.72 (m, 1H), 2.53 (m, 1H), 1.37 (m, 1H).

3.13.

Compound of the formula Ia in which A is N-phthalimido, n is 1 and $R^1$, $R^2$ and $R^3$ are hydrogen:

cis-Hydroxylation of the compound of Example 1.26.— carried out as described above—gives a 72% yield of (1RS,2SR,3RS,4SR)-2,3,4-trihydroxy-1-phthalimido-cyclopentane of melting point 175°–176° C. 1H NMR (270 MHz, $d_6$-DMSO), δ[ppm]: 7.9 (s, 4H), 4.9 (m, 2H), 4.6 (m, 3H), 3.73 (m, 2H), 2.05 (m, 2H).

3.14.

Compound of the formula Ia in which A is cytosin-1-yl, n is 2 and $R^1$, $R^2$ and $R^3$ are hydrogen:

cis-Hydroxylation of the compound of Example 1.28.2.— carried out as described above—with subsequent peracylation (acetic anhydride/pyridine/4-dimethylaminopyridine/ 20 hours/room temperature) of the triol formed gives an 83% yield of $N^4$-acetyl-1-[(1RS,2SR,3RS,4SR)-2,3,4-triacetoxy-cyclohex-1-yl]cytosine (compound of the formula Ia in which A is cytosin-1-yl, n is 2 and $R^1$-$R^3$ are acetyl) of melting point 226° C. 1H NMR (270 MHz, $d_6$-DMSO), δ[ppm]: 10.83 (s, 1H), 8.17 (d, 1H), 7.16 (d, 1H), 5.50 (m, 1H), 5.30 (m, 1H), 4.90 (m, 1H), 4.83 (m, 1H), 2.15 (s, 3H), 2.14 (s, 3H), 2.09 (s, 3H), 1.94–1.74 (m, 4H), 1.83 (s, 3H). This compound is dissolved in methanol, 40% strength aqueous methylamine is added and the mixture is boiled under reflux for 2 hours. 1-[(1RS,2SR,3RS,4SR)-2,3,4-Trihydroxy-cyclohex-1-yl]-cytosine of melting point 271° C. (decomposition) is obtained in a 94% yield. 1H NMR (270 MHz, $d_6$-DMSO), δ[ppm]: 7.48 (d, 1H), 6.86 (s, broad, 2H), 5.56 (d, 1H), 4.79 (d, 1H), 4.74 (d, 1H), 4.59 (m, 1H), 4.27 (d, 1H), 3.86 (m, 1H), 3.74 (m, 2H), 1.73 (m, 2H), 1.44 (m, 2H).

3.15.

Compound of the formula IIa, in which A is cytosin-1-yl and $R^1$, $R^2$ and $R^3$ are hydrogen:

cis-Hydroxylation of the compound of Example 2.17.— carried out as described above—gives a 65% yield of $N^4$-acetyl-1-[(1RS,2SR,3RS,6RS)-6-acetoxy-2,3-dihydroxy-cyclohex-1-yl]cytosine (compound of the formula VIIIa in which N is $N^4$-acetyl-cytosin-1-yl and $R^5$ is acetyl) of melting point 249° C. This compound is dissolved in methanol and the solution is heated under reflux with 40% strength aqueous methylamine to give, after working up of the reaction mixture, a 97% yield of 1-[(1RS,2SR,3RS,6RS)-2,3,6-trihydroxy-cyclohex-1-yl]-cytosine of melting point 304° C. (decomposition). 1H NMR (270 MHz, $d_6$-DMSO), δ[ppm]: 7.45 (d, 1H), 6.80 (s, broad, 2H), 5.58 (d, 1H), 4.79 (s, broad, 1H), 4.63 (m, 1H), 4.54 (d, 1H), 4.42 (d, 1H), 3.87 (m, 3H), 1.80 (m, 2H), 1.47 (m, 2H).

3.16.

Compound of the formula IIa in which A is uracil-1-yl and $R^1$, $R^2$ and $R^3$ are hydrogen:

cis-Hydroxylation of the compound of Example 1.29.1.—carried out as described above—gives a 72% yield of 1-[(1RS,2SR,3RS,6RS)-2,3,6-trihydroxy-cyclohex-1-yl] uracil of melting point 246° C. (recrystallized from ethanol). 1H NMR (270 MHz, $d_6$-DMSO), δ[ppm]: 11.12 (s, 1H), 7.51 (d, 1H), 5.49 (d, 1H), 4.67 (m, 2H), 4.56 (m, 1H), 3.88 (m, 3H), 3.18 (d, 1H), 1.70 (m, 2H), 1.48 (m, 2H).

Saturated Compounds

*Pneumocystis carinii*—Description of the experiment and results

Spraque-Dawley rats, 200–220 g, were collected into groups of 10 animals and treated with dexamethasone 1.5 mg/ml; of loxacin 0.2 mg/rat via the drinking water in order to induce the outbreak of pneumonia caused by *Pneumocystis carinii*.

After 7 weeks, the dexamethasone treatment was stopped and the preparation treatment was started.

Treatment was carried out every Monday, Wednesday and Friday for two weeks as follows:

TABLE I

| Group | Compound | Dose |
|---|---|---|
| 1. | Example 3.10.1 | 20 mg/kg oral |
| 2. | pentamidine | 20 mg/kg i.m. |
| 3. | pentamidine | 40 mg/kg i.m. |

After the two treatment weeks, a bronchial lavage was performed on the animals under Nembutal anesthesia.

The bronchial suspensions obtained were worked up and evaluated using the *Pneumocystis carinii* test kit from Progen Biotechnik GmbH, Heidelberg, Germany.

The results are summarized in Table II.

TABLE II

| Group | Reduction (%) |
|---|---|
| 1. | 22.9 |
| 2. | 37.7 |
| 3. | 16.9 |

In vitro experiments and results (antiviral action)

The antiviral activity of the compounds according to the invention was tested by in vitro experiments. For this, the compounds according to the invention were added in various dilutions to cell cultures of HeLa cells in microtiter plates. After 3 hours, the cultures were infected with the virus. HeLa cells were infected with vaccinia virus. 48–72 hours after the infection, the therapeutic result was determined microscopically from the cytopathic effect and photometrically after uptake of neutral red (Finter color test; Finter, N. B., in "Interferones" (N. B. Finter et al.), North Holland Publishing Co., Amsterdam (1966)). The minimum concentration at which about half the cells exhibit no cytopathogenic effect is regarded as the minimum inhibitory concentration (MIC). The results are summarized in Table III.

(DTM=dosis rolerata maxima)

TABLE III

| Compound from Example | Vaccinia | |
|---|---|---|
| 3.1.1 | MIC: | 0.05 µg/ml |
| | DTM: | >400 µg/ml |
| 3.3 | MIC: | 44.4 µg/ml |
| | DTM: | >400 µg/ml |

We claim:

1. A compound of the formula VIIa or VIIIa:

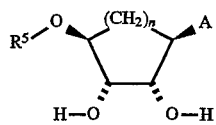
VIIa

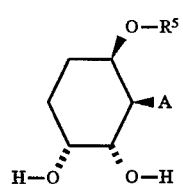
VIIIa wherein $R^5$ is hydrogen n is 1 or 2 and
A is
  adenin-9-yl,
  adenin-3-yl,
  {$N^6$-(N-methyl-2-pyrrolidin-yliden)}adenin-9-yl,
  adenin-$N^1$-Oxid-9-yl,
  hypoxanthin-9-yl
  6-chlorpurin-9-yl,
  6-chlorpurin-7-yl,
  adenin-7-yl,
  6-(2,2-diphenyl-ethylamino)-purin-9-yl,
  2,6-diaminopurin-9-yl,
  2-amino-6-mercapto-purin-9-yl
  2-aminopurin-9-yl,
  guanin-9-yl,
  guanin-7-yl,
  $N^2$-acetyl -6-O-di-phenylcarbamoyl-guanin-7-yl,
  $N^6$-acetyl-adenin-9-yl,
  2-acetamido-6-ethoxy-purin-9-yl, or
  $N^6$-methyl-adenin-9-yl;
  and when n is 2, A can also be 2-amino-6-chloro-purin-9-yl.

2. A pharmaceutical composition containing at least one compound of the Formulas VIIa or VIIIa:

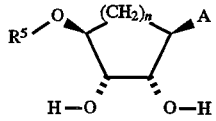
VIIa

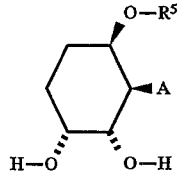
VIIIa wherein $R^5$ is hydrogen n is 1 or 2 and
A is
  adenin-9-yl,
  adenin-3-yl,
  {$N^6$-(N-methyl-2-pyrrolidin-yliden)}adenin-9-yl,
  adenin-$N^1$-Oxid-9-yl, hypoxanthin-9-yl
6-chlorpurin-9-yl,
6-chlorpurin-7-yl,
adenin-7-yl,
6-(2,2-diphenyl-ethylamino)-purin-9-yl,
2,6-diaminopurin-9-yl,
2-amino-6-mercapto-purin-9-yl
2-aminopurin-9-yl,
guanin-9-yl,
guanin-7-yl, $N^2$-acetyl-6-O-di-phenylcarbamoyl-guanin-7-yl,
$N^6$-acetyl-adenin-9-yl,
2-acetamido-6-ethoxy-purin-9-yl, or
$N^6$-methyl-adenin-9-yl; and when n is 2, N can also be 2-amino-6-chloro-purin-9-yl; or a physiologically tolerated salt of said compound, together with a pharmaceutically acceptable carrier.

* * * * *